(12) United States Patent
Inatsugi et al.

(10) Patent No.: US 11,078,211 B2
(45) Date of Patent: *Aug. 3, 2021

(54) PHOTORESPONSIVE NUCLEOTIDE ANALOG CAPABLE OF PHOTOCROSSLINKING IN VISIBLE LIGHT REGION

(71) Applicants: JAPAN ADVANCED INSTITUTE OF SCIENCE AND TECHNOLOGY, Nomi (JP); NICCA CHEMICAL CO., LTD., Fukui (JP)

(72) Inventors: Takahiro Inatsugi, Fukui (JP); Ayako Koto, Fukui (JP); Isao Ishimaru, Fukui (JP); Masahiko Takamura, Fukui (JP); Kenzo Fujimoto, Nomi (JP)

(73) Assignees: JAPAN ADVANCED INSTITUTE OF SCIENCE AND TECHNOLOGY, Ishikawa (JP); NICCA CHEMICAL CO., LTD., Fukui (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/629,148

(22) PCT Filed: Jul. 19, 2018

(86) PCT No.: PCT/JP2018/027169
§ 371 (c)(1),
(2) Date: Jan. 7, 2020

(87) PCT Pub. No.: WO2019/021945
PCT Pub. Date: Jan. 31, 2019

(65) Prior Publication Data
US 2020/0317685 A1    Oct. 8, 2020

(30) Foreign Application Priority Data

Jul. 26, 2017 (JP) .............. JP2017-144935

(51) Int. Cl.
*C07D 491/052* (2006.01)
*C07F 9/6561* (2006.01)

(52) U.S. Cl.
CPC ........ *C07D 491/052* (2013.01); *C07F 9/6561* (2013.01)

(58) Field of Classification Search
CPC .............. C07D 491/052; C07F 9/6561
See application file for complete search history.

(56) References Cited

U.S. PATENT DOCUMENTS

| | | | | |
|---|---|---|---|---|
| 5,082,934 A * | 1/1992 | Saba | ............. | C07H 21/00 536/17.2 |
| 6,005,094 A * | 12/1999 | Simon | ............. | C07H 21/00 435/6.14 |
| 10,450,334 B2 * | 10/2019 | Fujimoto | ............. | C07H 21/00 |
| 2010/0274000 A1 | 10/2010 | Fujimoto et al. | | |
| 2011/0034683 A1 | 2/2011 | Fujimoto et al. | | |
| 2016/0031918 A1 | 2/2016 | Fujimoto et al. | | |
| 2016/0326207 A1 | 11/2016 | Fujimoto et al. | | |
| 2020/0172563 A1 * | 6/2020 | Fujimoto | ............. | C07H 19/23 |

FOREIGN PATENT DOCUMENTS

| | | |
|---|---|---|
| CN | 107163169 A | 9/2017 |
| EP | 2 216 338 | 8/2010 |
| EP | 2 980 073 | 2/2016 |
| EP | 3660021 | 6/2020 |
| JP | 4-506206 | 10/1992 |
| JP | 5-507419 | 10/1993 |
| JP | 2001-348398 | 12/2001 |
| JP | 3753938 B2 | 3/2006 |
| JP | 3753942 B2 | 3/2006 |
| JP | 4814904 B2 | 11/2011 |
| JP | 4940311 B2 | 5/2012 |
| JP | 5925383 B2 | 5/2016 |
| WO | 92/02532 | 2/1992 |
| WO | 2005/083073 | 9/2005 |
| WO | 2009/066447 | 5/2009 |
| WO | 2010/147673 | 12/2010 |
| WO | 2014/157565 A1 | 10/2014 |

(Continued)

OTHER PUBLICATIONS

Fujimoto; RSC Advances 2019, 9, 30693-30697. (Year: 2019).*
Gupta; Journal of Biotechnology 2017, 259, 148-159. (Year: 2017).*
Haque; Angew. Chem. Int. Ed. 2014, 53, 7001-7005. (Year: 2014).*
Kean; Biochemistry, 1988, 27, 26, 9113-9121. (Year: 1988).*

(Continued)

*Primary Examiner* — Daniel R Carcanague

(74) *Attorney, Agent, or Firm* — Wenderoth, Lind & Ponack, L.L.P.

(57) ABSTRACT

Provided are a compound represented by the following formula I; a novel photoreactive compound that can be used in nucleic acid photoreaction techniques by a photoreactive crosslinking agent comprising the compound; and a photoreactive crosslinking agent in which the photoreactive compound is used.

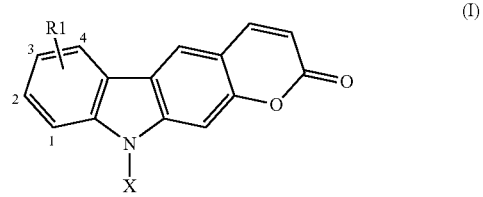

(I)

10 Claims, 13 Drawing Sheets

Specification includes a Sequence Listing.

(56) References Cited

FOREIGN PATENT DOCUMENTS

| WO | WO-2019022158 A1 | * | 1/2019 | ......... C07D 491/052 |
|---|---|---|---|---|
| WO | WO2020158687 | * | 8/2020 | |

OTHER PUBLICATIONS

Lee; Biochemistry 1988, 27, 3197-3203. (Year: 1988).*
Sakamoto; Org. Lett. 2015, 17, 4, 936-939. (Year: 2015).*
Yoshimura; Org. Lett. 2008, 10, 15, 3227-3230. (Year: 2008).*
Gia; J Photochem Photobiol B. 1988, 2, 435-442. DOI: 10.1016/1011-1344(88)85072-3 (Year: 1988).*
Notification of Transmittal of Translation of the International Preliminary Report on Patentabililty (Form PCT/IB/338) issued in counterpart International Application No. PCT/JP2018/027169 dated Feb. 6, 2020 with Forms PCT/IB/373 and PCT/ISA/237. (5 pages).
Gia, O. et al. ; "Pyrrolocoumarin derivatives: DNA-binding properties", Journal of Photochemistry and Photobiology, B: Biology, 1988, 2, pp. 435-442, (8 pages), cited in ISR.
Vronteli, A. et al.; "Synthesis of fused pyranocarbazolones with biological interest", ARKIVOC, 2015, (3), pp. 111-123, (13 pages), cited in ISR.
Rodighiero, P. et al.; "Pynrolocoumarin Derivatives as Potential Photoreagents Toward DNA", Journal of Heterocyclic Chemistry, 1987, 24(4), pp. 1041-1043, (3 pages), cited in ISR.
Fujimoto, K. et al.; "DNA Photo-cross-linking Using Pyranocarbazole and Visible Light", Organic Letters, 2018. 04. 27, 20(10), pp. 2802-2805 (4 pages), cited in ISR.
Nakamura, S. et al.; "Rapid Photopolymerization of Oligodeoxynucleotieds by 3-Cyanovinylcarbazole mediated DNA Photocrossilinking", Journal of Photopolymer and Technology, vol. 27, No. 4(2014), pp. 485-490 (6 pages), cited in specification.
International Search Report dated Oct. 2, 2018, issued in counterpart International Application No. PCT/JP2018/027169 (2 pages).
Extended (supplementary) European Search Report dated Oct. 31, 2016, issued in European Patent Application No. 14773781.1. (6 pages).
Notification of Transmittal of Translation of the International Preliminary Report on Patentability (Form PCT/IB338) issued in counterpart International Application No. PCT/JP2014/058988. (16 pages). dated Sep. 28, 2015.
International Search Report dated Jun. 10, 2014, issued in Application No. PCT/JP2014/058988 (2 pages).
International Search Report dated Aug. 28, 2018, issued in International Application No. PCT/JP2018/027961. (2 pages).
Notification of Transmittal of Translation of the International Preliminary Report on Patentability (PCT/IPEA/Form 409) of International Application No. PCT/JP2018/027961 dated Jan. 30, 2020 (4 pages).
Kashida et al., "Control of the Chirality and Helicity of Oligomers of Serinol Nucleic Acid (SNA) by Sequence Design" Agnew. Chem. Int. Ed. 2011, vol. 50, pp. 1285-1288 (2011).
Extended European Search Report dated Feb. 17, 2021 in corresponding European Patent Application No. 18837260,1.
Extended European Search Report dated Mar. 24, 2021 in corresponding European Patent Application No. 18838876.3.

* cited by examiner

[FIG. 1]
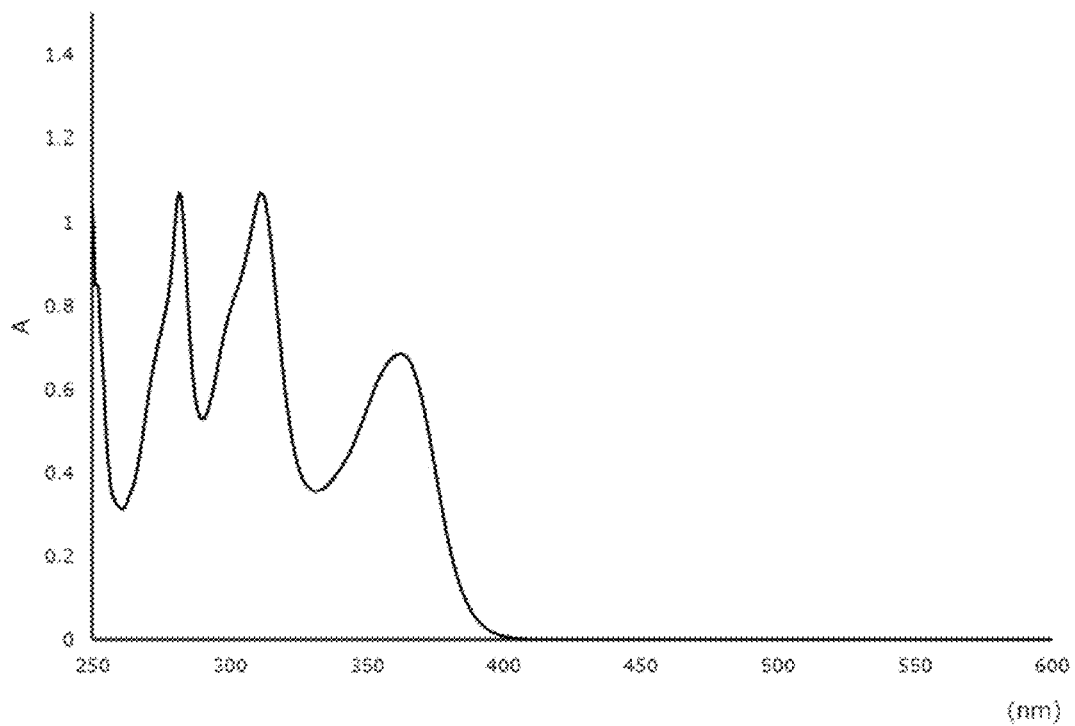

[FIG. 2]
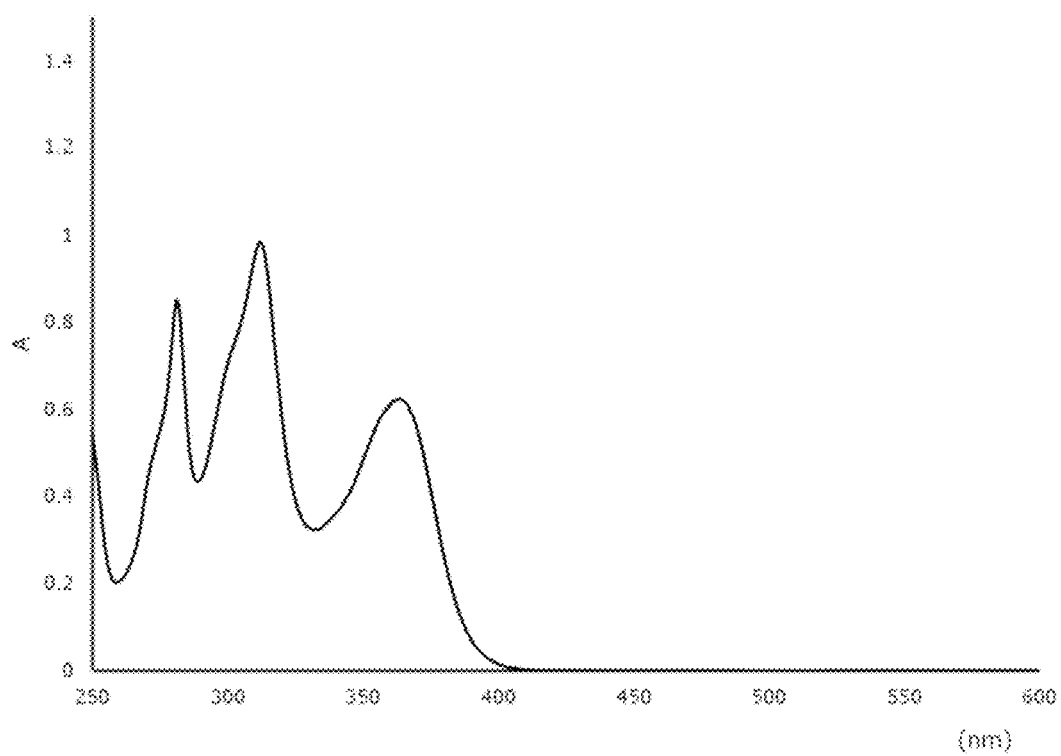

FIG 3a
ODN(A-pc-D)  X=pc-D
5'-TGCAXCCGT-3'  SEQ ID NO: 1
ODN(T)
3'-ACGTGGGCA-5'  SEQ ID NO: 2
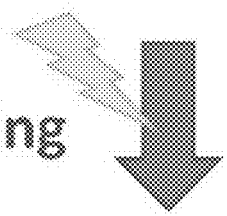
Photo-crosslinking
Double-Stranded DNA Photocrosslink (❋) ODN (pc-D/T)
5'-TGCAXCCGT-3'
3'-ACGTGGGCA-5'

[FIG. 3b]
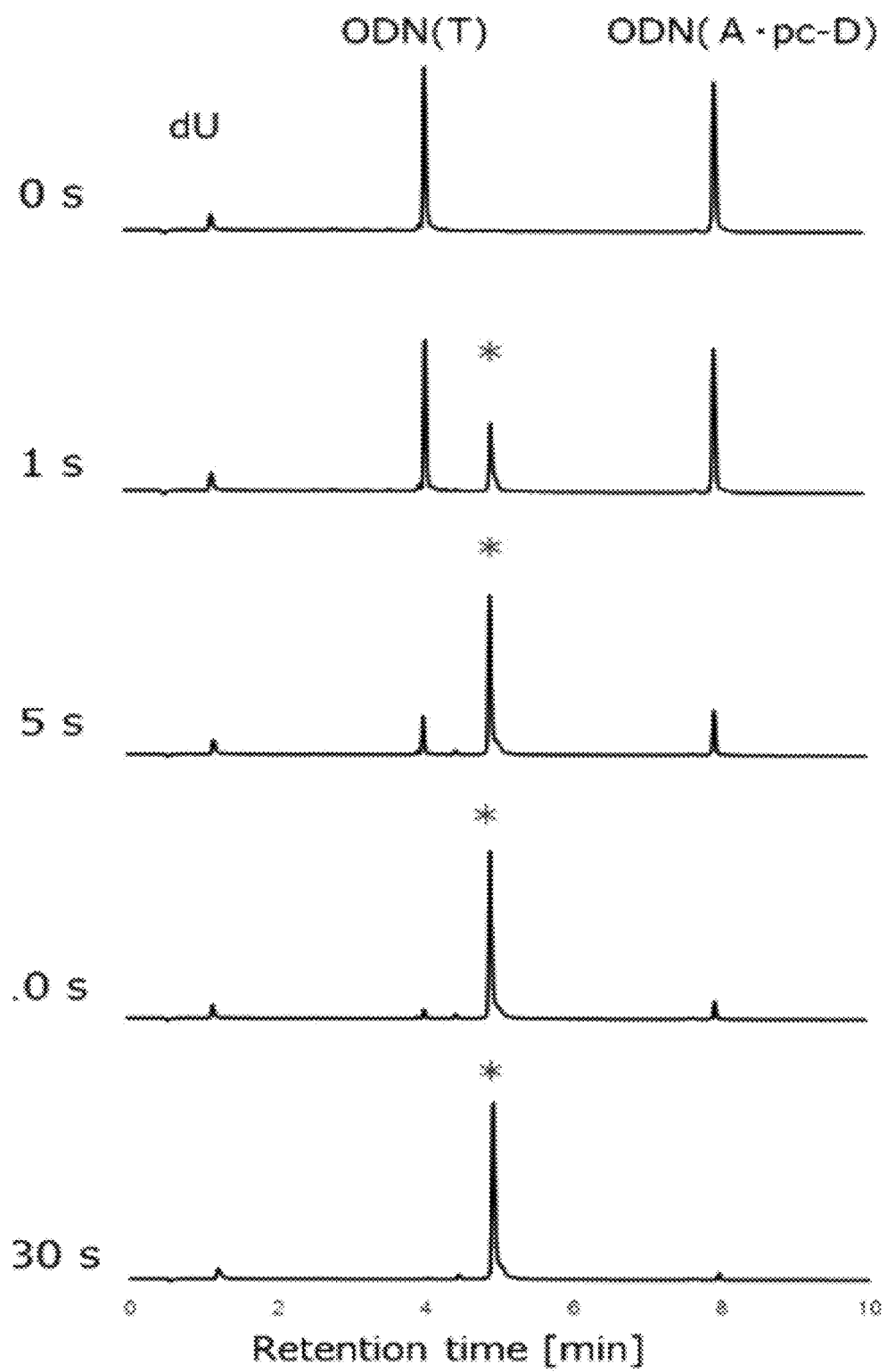

[FIG. 3c]
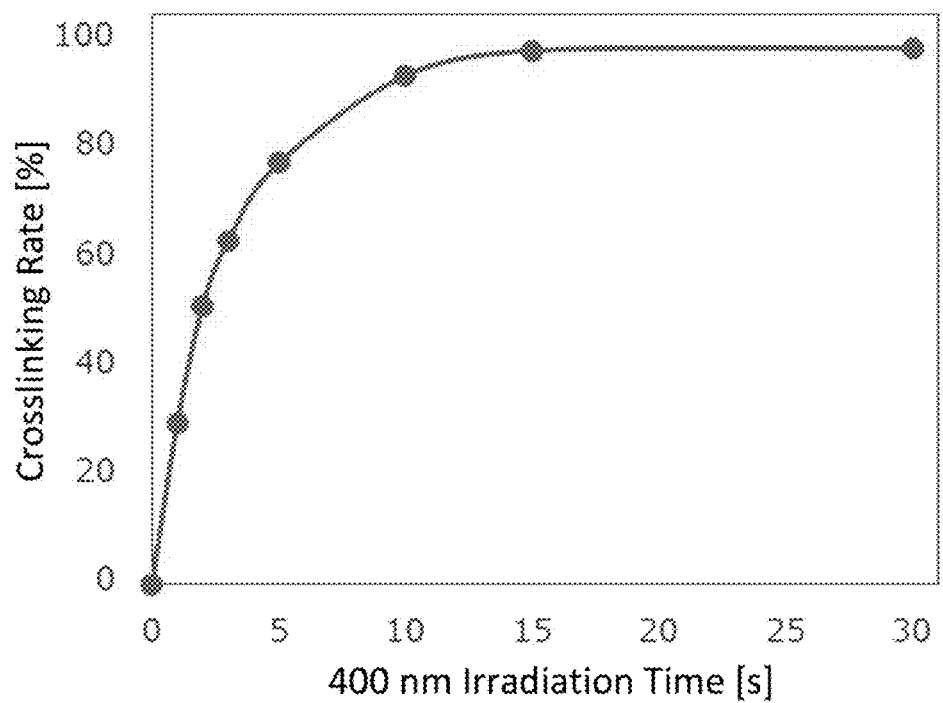

[FIG. 3d]
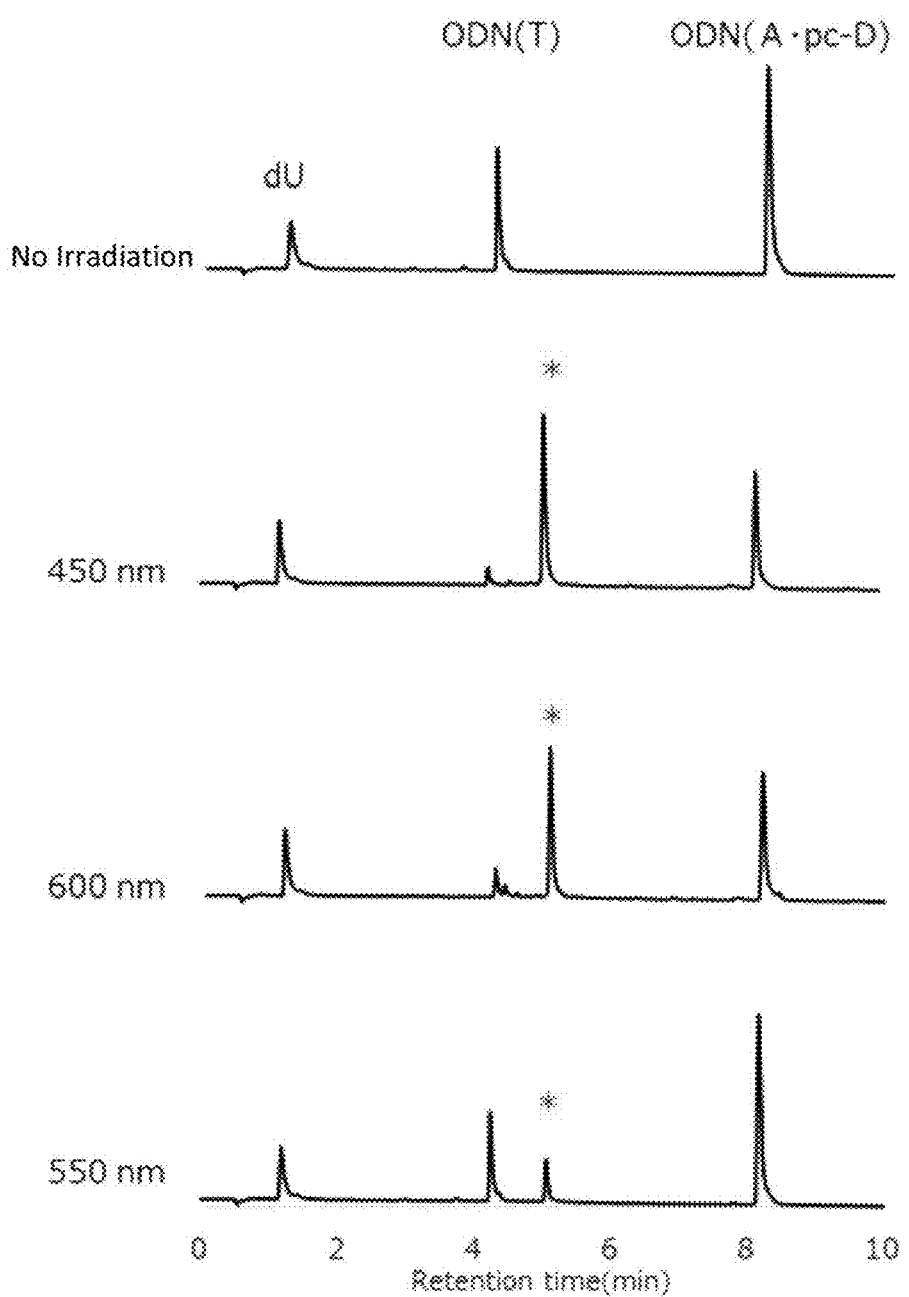

FIG. 4a
ODN(G·pc-D)  X=pc-D
5'-TGCGXCCGT-3'   SEQ ID NO: 3
ODN(C)
3'-ACGCGGGCA-5'   SEQ ID NO: 4
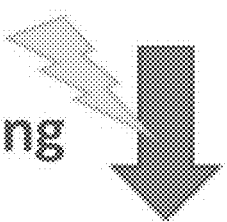
Double-Stranded DNA Photocrosslink (*) ODN (pc-D/C)
5'-TGCGXCCGT-3'
3'-ACGCGGGCA-5'

[FIG. 4b]
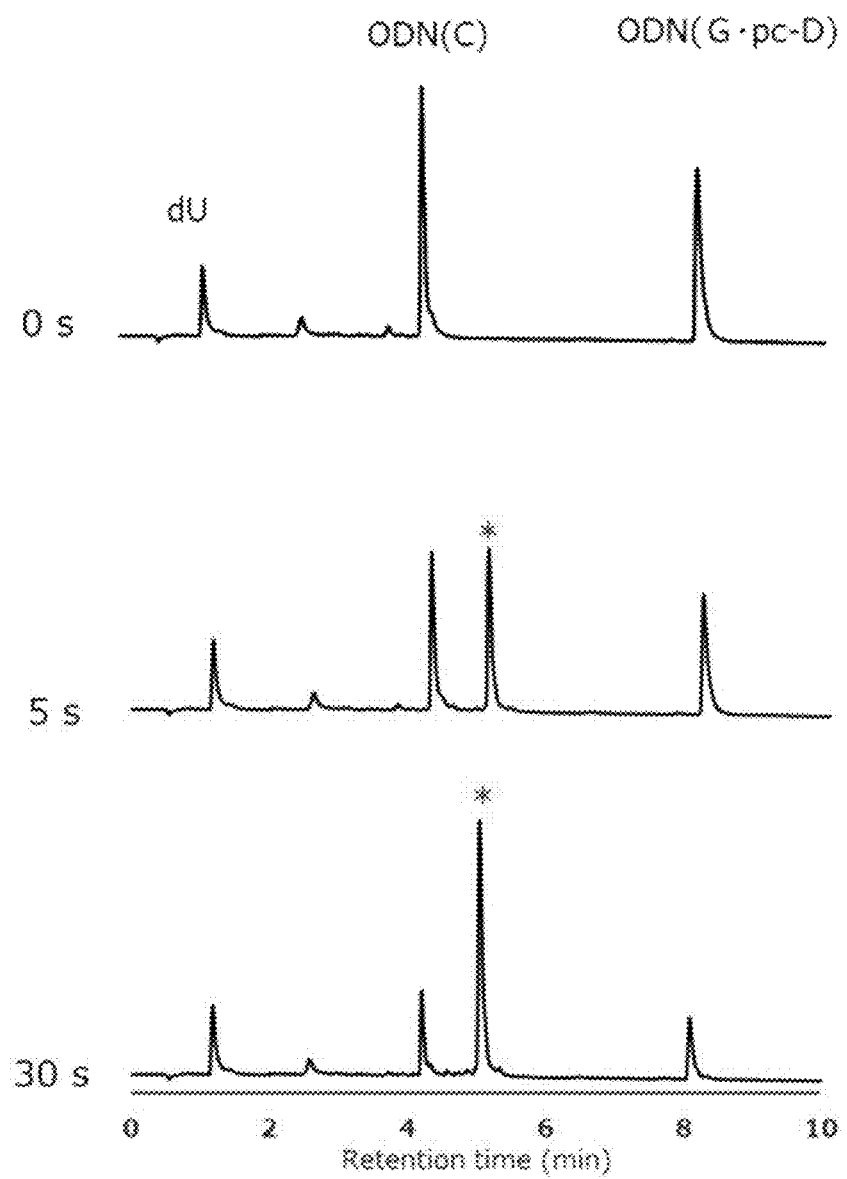

FIG. 5a
Double-Stranded DNA Photocrosslink (*) ODN (pc-D/T)
5'-TGCAXCCGT-3'
3'-ACGTGGGCA-5'
Photo-cleavage
ODN(A·pc-D) X=pc-D
5'-TGCAXCCGT-3'     SEQ ID NO: 1
ODN(T)
3'-ACGTGGGCA-5'     SEQ ID NO: 2

[FIG. 5b]
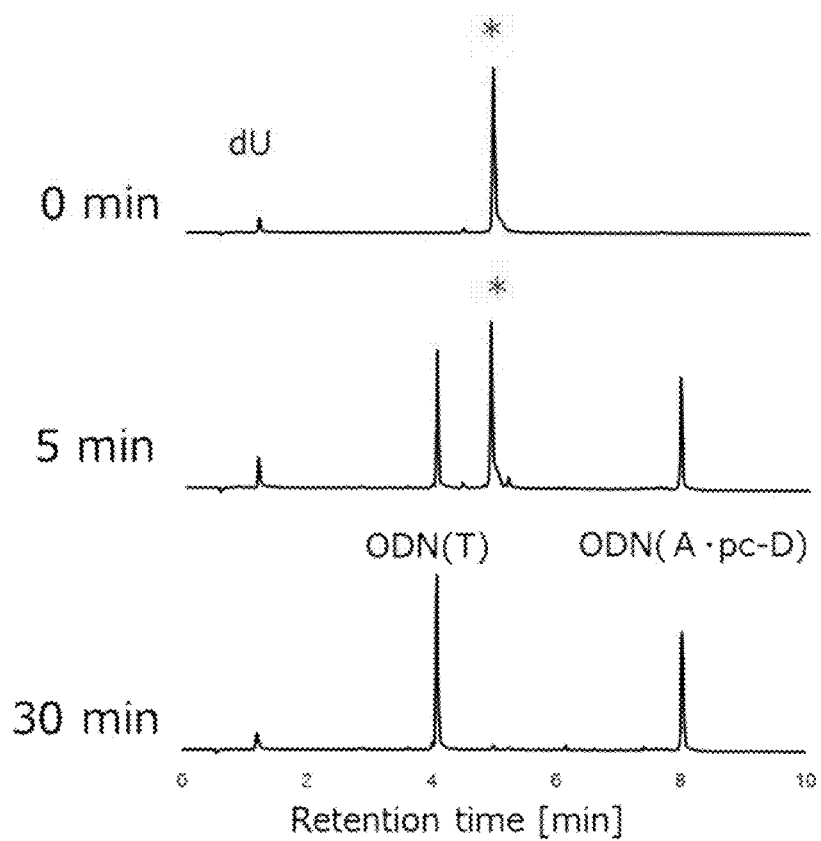

FIG. 6a
ODN(A·pc-S)  X=pc-S
5'-TGCAXCCGT-3'   SEQ ID NO: 5
ODN(T)
3'-ACGTGGGCA-5'   SEQ ID NO: 2
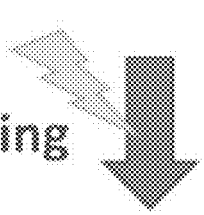
Photo-crosslinking
Double-Stranded DNA Photocrosslink (*) ODN (pc-S/T)
5'-TGCAXCCGT-3'
3'-ACGTGGGCA-5'

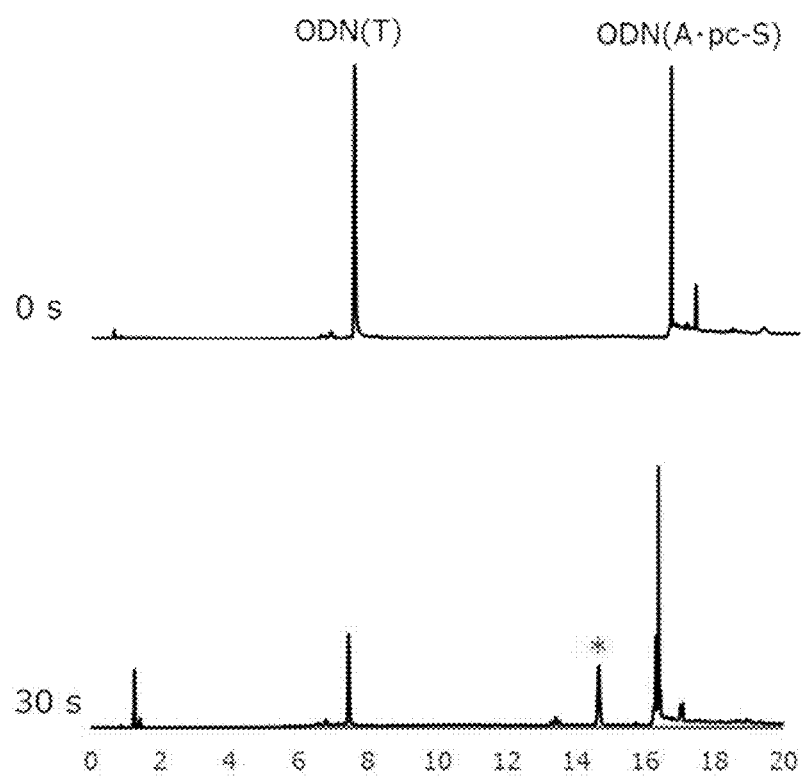
[FIG. 6b]

[FIG. 7]
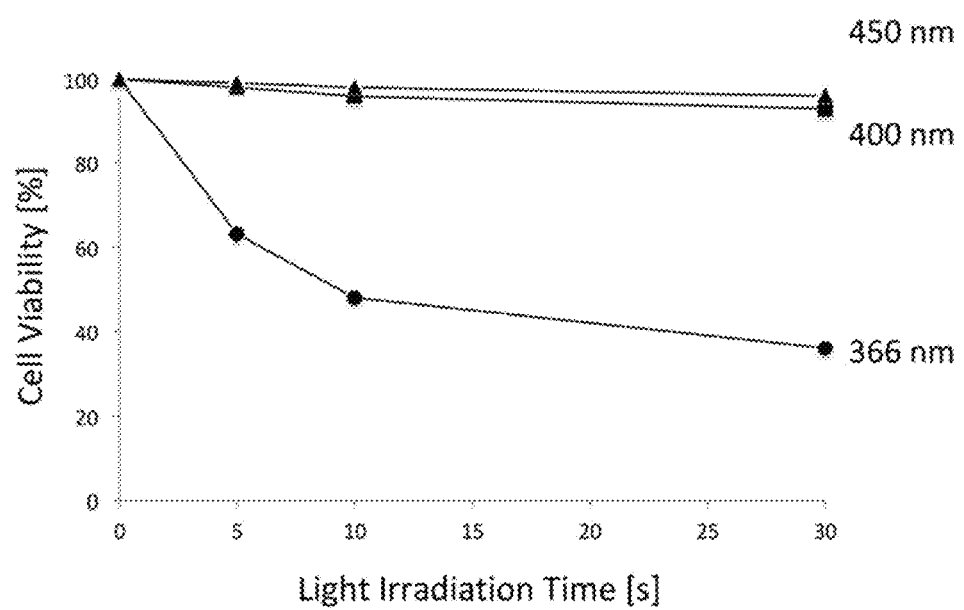

SEQUENCE LISTING

```
<160> NUMBER OF SEQ ID NOS: 5

<210> SEQ ID NO 1
<211> LENGTH: 9
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Artificial Sequence including pc-D
<220> FEATURE:
<221> NAME/KEY: misc_feature
<222> LOCATION: (5)..(5)
<223> OTHER INFORMATION: n is pc-D

<400> SEQUENCE: 1 tgcanccgt                                                               9

<210> SEQ ID NO 2
<211> LENGTH: 9
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Complementary to ODN(A pc-D)

<400> SEQUENCE: 2 acgggtgca                                                               9

<210> SEQ ID NO 3
<211> LENGTH: 9
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Artificial Sequence including pc-D
<220> FEATURE:
<221> NAME/KEY: misc_feature
<222> LOCATION: (5)..(5)
<223> OTHER INFORMATION: n is pc-D

<400> SEQUENCE: 3 tgcgnccgt                                                               9

<210> SEQ ID NO 4
<211> LENGTH: 9
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Complementary to ODN(G pc-D)

<400> SEQUENCE: 4 acgggcgca                                                               9

<210> SEQ ID NO 5
<211> LENGTH: 9
<212> TYPE: DNA
<213> ORGANISM: Artificial Sequence
<220> FEATURE:
<223> OTHER INFORMATION: Chemically Synthesized
<220> FEATURE:
<223> OTHER INFORMATION: Artificial Sequence including pc-S
<220> FEATURE:
<221> NAME/KEY: misc_feature
<222> LOCATION: (5)..(5)
<223> OTHER INFORMATION: n is pc-S
```

```
<400> SEQUENCE: 5 tgcanccgt                                                        9
```

PHOTORESPONSIVE NUCLEOTIDE ANALOG CAPABLE OF PHOTOCROSSLINKING IN VISIBLE LIGHT REGION

TECHNICAL FIELD

The present invention relates to a photoresponsive nucleotide analog capable of photocrosslinking in visible light region.

BACKGROUND ART

Basic techniques in the field of molecular biology include ligation of nucleic acids and crosslinking of nucleic acids. The ligation or crosslinking of nucleic acids are used for introduction of genes or detection of nucleotide sequences, or inhibition of gene expressions, for example, in combination with hybridization. Therefore, the techniques of the ligation and crosslinking of nucleic acids are very important techniques that are used in basic molecular biology researches, as well as, for example, diagnosis or treatment in the medical field, or development or production of therapeutic agents and diagnostic agents, or development or production of enzymes, microorganisms or the like in the industrial and agricultural fields.

Known as photoreaction techniques of nucleic acids are photoligation techniques using 5-cyanovinyldeoxyuridine (Patent Document 1: Japanese Patent No. 3753938 B, Patent Document 2: Japanese Patent No. 3753942 B); and photocrosslinking techniques using modified nucleosides having a 3-vinylcarbazole structure at the base site (Patent Document 3: Japanese Patent No. 4814904 B, Patent Document 4: Japanese Patent No. 4940311 B). Further, there is a photocrosslinking technique using a compound in which a so-called sugar moiety structure of a modified nucleoside having a 3-vinylcarbazole structure at the base site is substituted with a chain alkylamide (Patent Document 5: Japanese Patent No. 5925383 B).

Furthermore, it has recently become possible to construct various nanostructures using the ability of nucleic acids to form double strands, and the ligation and crosslinking techniques have become important in the field of nanotechnology. For example, Non-Patent Document 1 discloses a technique for providing heat resistance to a nano-sheet consisting of oligo DNAs by photocrosslinking of nucleic acids.

CITATION LIST

Patent Literatures

Patent Document 1: Japanese Patent No. 3753938 B
Patent Document 2: Japanese Patent No. 3753942 B
Patent Document 3: Japanese Patent No. 4814904 B
Patent Document 4: Japanese Patent No. 4940311 B
Patent Document 5: Japanese Patent No. 5925383 B

Non-Patent Literature

Non-Patent Document 1: J. Photopol. S. Tech., 2014, 27, 485

SUMMARY OF INVENTION

Technical Problem

Because of the importance of the photoreaction technique of nucleic acids, there is a further need for novel compounds that can be used for the photoreaction technique of nucleic acids. An object of the present invention is to provide a novel photoreactive compound that can be used for a photoreaction technique of nucleic acids, and a photoreactive crosslinking agent using the photoreactive compound.

Solution to Problem

As a result of intensive studies for photoreactive compound that will be photoreactive crosslinking agent capable of being used for the photoreaction technique of nucleic acids, the present inventors have found that a compound having a pyranocarbazole skeleton structure in place of a base moiety of a nucleic acid and having a skeleton structure represented by the formula I as described later in place of ribose and deoxyribose moieties will be such a photoreactive crosslinking agent capable of being used for the photoreaction technique of nucleic acids, and have arrived at the present invention.

A photoreactive crosslinking agent according to the present invention has a feature capable of being photocrosslinked by irradiation with light having a wavelength longer than that of the conventional one, for example, irradiation with light in the visible light region, which feature is derived from the above structure. Therefore, when it is desired to avoid any damage to DNAs and cells as much as possible, the photoreactive crosslinking agent according to the present invention is particularly advantageous because it can be photocrosslinked by irradiation with light having a long wavelength.

It should be noted that the photoreactive compound according to the present invention initiates a photoreaction by light irradiation, but the term "photoreactive" may be referred to as "photoresponsive" for emphasizing the meaning that a compound which has previously been stable initiates reaction in response to a signal of the light irradiation.

Therefore, the present invention includes the following aspects (1) to (8):

(1)

A compound represented by the following formula I:

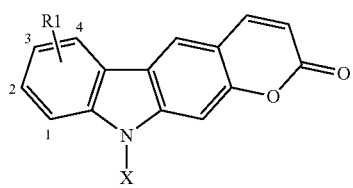

(I)

in which formula I:

R1 is a group selected from the group consisting of a hydrogen atom, a halogen atom, a methyl group, a methyl fluoride group, an ethyl group, an ethyl fluoride group, and a C1-C3 alkylsulfanyl group;

X is a group represented by the following formula Is or IIs:

(Is)

in which formula Is:
R11 and R12 are each independently a group selected from the group consisting of a hydrogen atom, a C1-C3 alkyl group, and a C1-C3 alkoxy group;
na is 1 or 2;
R21 and R22 are each independently a group selected from the group consisting of a hydrogen atom, a C1-C3 alkyl group, and a C1-C3 alkoxy group;
nb is 0 or 1;
R31 and R32 are each independently a group selected from the group consisting of a hydrogen atom, a C1-C3 alkyl group, and a C1-C3 alkoxy group;
nc is 0, 1, 2 or 3, and nc+nd is an integer of 0 to 3;
R41 and R42 are each independently a group selected from the group consisting of a hydrogen atom, a C1-C3 alkyl group, and a C1-C3 alkoxy group;
nd is 0, 1, 2 or 3, and nc+nd is an integer of 0 to 3;
Q1 is a group selected from the group consisting of:
a hydrogen atom;
a phosphate group formed together with O bonded to Q1;
a nucleotide, nucleic acid or peptide nucleic acid linked via a phosphodiester bond formed by a phosphate group formed together with O bonded to Q1; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;
Q2 is a group selected from the group consisting of:
a hydrogen atom;
a phosphate group formed together with O bonded to Q2;
a nucleotide, nucleic acid or peptide nucleic acid linked via a phosphodiester bond formed by a phosphate group formed together with O bonded to Q2; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH; or (IIs)

in which formula IIs:
R51 and R52 are each independently a group selected from the group consisting of a hydrogen atom, a C1-C3 alkyl group, and a C1-C3 alkoxy group;
ne is 1, 2 or 3;
R61 and R62 are each independently a group selected from the group consisting of a hydrogen atom, a C1-C3 alkyl group, and a C1-C3 alkoxy group;
nf is 0, 1, 2 or 3;
Q1 is a groups selected from the group consisting of:
a hydrogen atom;
a phosphate group formed together with O bonded to Q1;
a nucleotide, nucleic acid or peptide nucleic acid linked via a phosphodiester bond formed by a phosphate group formed together with O bonded to Q1; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;
Q2 is group selected from the group consisting of:
a hydrogen atom;
a phosphate group formed together with O bonded to Q2;
a nucleotide, nucleic acid or peptide nucleic acid linked via a phosphodiester bond formed by a phosphate group formed together with O bonded to Q2; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH.

(2)
The compound according to (1), wherein X is a group represented by the following formula It:

(It)

in which formula It:
R11 and R12 are each independently the group as defined in the formula Is;

R31 and R32 are each independently the group as defined in the formula Is;
R41 and R42 are each independently the group as defined in the formula Is; and
Q1 and Q2 are the groups as defined in the formula Is.

(3) The compound according to (1), wherein X is a group represented by the following formula Iu:

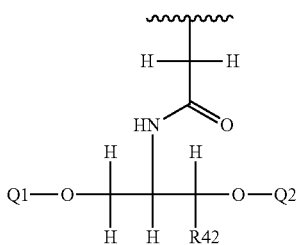

(Iu)

in which formula Iu:
R42 is the group as defined in the formula Is; and Q1 and Q2 are the groups as defined in the formula Is.

(4) The compound according to (3), wherein R42 is a hydrogen atom or a methyl group.

(5) A photoreactive crosslinking agent, comprising the compound according to any one of (1) to (4).

(6) A reagent for producing photoreactive modified nucleic acids, comprising the compound according to any one of (1) to (4).

(7) A method for forming a photocrosslink between a photoreactive crosslinking agent and a nucleic acid base having a pyrimidine ring using a photoreactive crosslinking agent comprising the compound according to any one of (1) to (4).

(8) A method for producing a compound represented by the following formula V, comprising subjecting a compound represented by the following formula III:

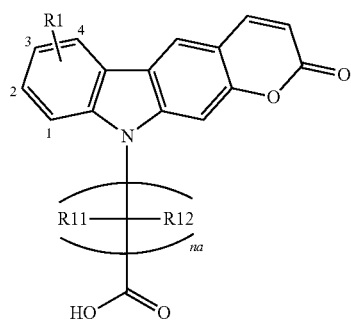

(III)

in which formula III:
R1 is a group selected from the group consisting of a hydrogen atom, a halogen atom, a methyl group, a methyl fluoride group, an ethyl group, an ethyl fluoride group, and a C1-C3 alkylsulfanyl group;

R11 and R12 are each independently a group selected from the group consisting of a hydrogen atom, a C1-C3 alkyl group, and a C1-C3 alkoxy group; and
na is 1 or 2,
to dehydration condensation with a compound represented by the formula IV:

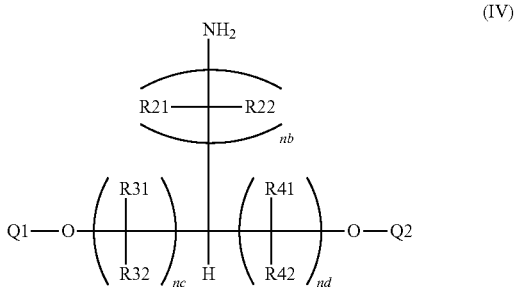

(IV)

in which formula IV:
R21 and R22 are each independently a group selected from the group consisting of a hydrogen atom, a C1-C3 alkyl group, and a C1-C3 alkoxy group;
nb is 0 or 1;
R31 and R32 are each independently a group selected from the group consisting of a hydrogen atom, a C1-C3 alkyl group, and a C1-C3 alkoxy group;
nc is 0, 1, 2 or 3, and nc+nd is an integer of 0 to 3;
R41 and R42 are each independently a group selected from the group consisting of a hydrogen atom, a C1-C3 alkyl group, and a C1-C3 alkoxy group;
nd is 0, 1, 2 or 3, and nc+nd is an integer of 0 to 3;
Q1 is a group selected from the group consisting of:
a hydrogen atom;
a phosphate group formed together with O bonded to Q1;
a nucleotide, nucleic acid or peptide nucleic acid linked via a phosphodiester bond formed by a phosphate group formed together with O bonded to Q1; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and benzoyl group;
Q2 is s group selected from the group consisting of:
a hydrogen atom;
a phosphate group formed together with O bonded to Q2;
a nucleotide, nucleic acid or peptide nucleic acid linked via a phosphodiester bond formed by a phosphate group formed together with O bonded to Q2; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH, to provide a compound represented by the formula V:

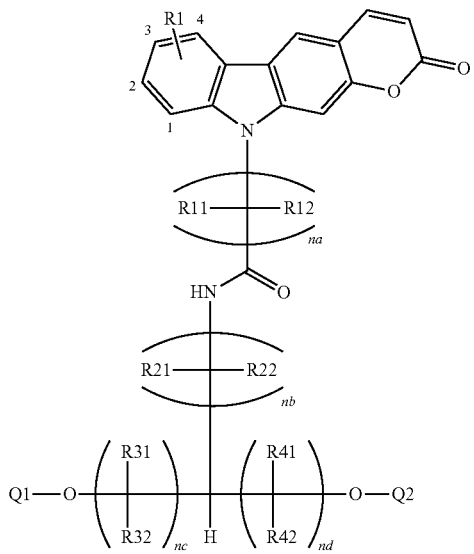

(V)

in which formula V:

R1, R11 and R12 are each independently the group as defined in the formula III;

na is the integer as defined in the formula III;

R21, R22, R31, R32, R41, R42, Q1 and Q2 are each independently the group as defined in the formula IV; and nb, nc, and nd are each independently the integer as defined in the formula IV.

Advantageous Effects of Invention

The present invention provides a novel compound that will be a photoreactive crosslinking agent capable of being used for a photoreaction technique of nucleic acids. This is due to a novel chemical structure having neither a natural sugar structure nor a base structure. According to the compound of the present invention, a photocrosslink can be formed by irradiation with light having a longer wavelength than the conventional photoreactive crosslinking agent, so that an inverse effect of irradiation with light on nucleic acids and cells can be minimized.

BRIEF DESCRIPTION OF DRAWINGS

FIG. 1 is a UV-vis spectrum of Compound 5.

FIG. 2 is a UV-vis spectrum of Compound 8.

FIG. 3a is an explanatory diagram showing a flow of operations for photocrosslinking thymine, illustrating SEQ ID NO: 1 and complementary SEQ ID NO: 2.

FIG. 3b is a diagram showing results of HPLC analysis of a product obtained by irradiation with light.

FIG. 3c is a graph showing a change of a crosslinking rate as a function of light irradiation time.

FIG. 3d is a diagram showing results of HPLC analysis of a product obtained by irradiation with light having each wavelength.

FIG. 4a is an explanatory diagram showing a flow of operations for photocrosslinking cytosine, illustrating SEQ ID NO: 3 and complementary SEQ ID NO: 4.

FIG. 4b is a diagram showing results of HPLC analysis of a product as a function of each light irradiation time.

FIG. 5a is an explanatory diagram showing a flow of operations for cleaving a photocrosslink, illustrating SEQ ID NO: 1 and complementary SEQ ID NO: 2.

FIG. 5b is a diagram showing results of HPLC analysis of a cleaved product as a function of each light irradiation time.

FIG. 6a is an explanatory diagram showing a flow of operations for forming a photocrosslink by pc-S, illustrating SEQ ID NO: 5 and complementary SEQ ID NO: 2.

FIG. 6b is a diagram showing results of HPLC analysis of a product by irradiation with light.

FIG. 7 is a graph comparing light irradiation time (seconds) with cell viability (%) at each wavelength.

DESCRIPTION OF THE PREFERRED EMBODIMENTS

The present invention will be described below in detail by providing specific embodiments. The present invention is not limited to the following specific embodiments as mentioned below.

[Structure of Compound]

The present invention relates to a compound represented by the formula I:

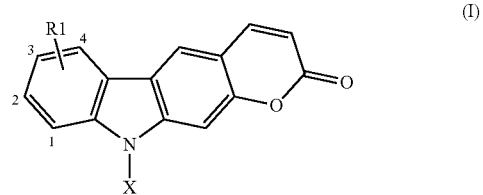

(I)

In the formula I, R1 is a group selected from the group consisting of a hydrogen atom, a halogen atom, a methyl group, a methyl fluoride group, an ethyl group, an ethyl fluoride group, and a C1-C3 alkylsulfanyl group. R1 is preferably a hydrogen atom, a halogen atom, a methyl group, or an ethyl group, and particularly preferably a hydrogen atom. The formula I shows that R1 may be substituted and linked to a hydrogen atom bonded to the carbon at any of positions 1, 2, 3, and 4 as carbon positions numbered to the carbon atoms of the ring to which R1 is bonded. In a preferred embodiment, R1 can be bonded to the carbon atom at position 3.

In the formula I, X is a group represented by the following formula Is or formula IIs:

(Is)

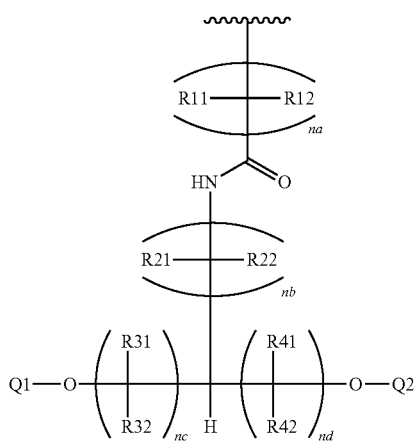

In the formula Is, R11 and R12 are each independently a group selected from the group consisting of a hydrogen atom, a C1-C3 alkyl group, and a C1-C3 alkoxy group. Preferably, R11 and R12 are each independently a hydrogen atom or a methyl group, and particularly preferably a hydrogen atom. The symbol na is an integer indicating the number of a repeating unit, and is 1 or 2, and preferably 1. R11 and R12 can be each independently the above group in each repeating unit.

In the formula Is, R21 and R22 are each independently a group selected from the group consisting of a hydrogen atom, a C1-C3 alkyl group, and a C1-C3 alkoxy group. Preferably, R21 and R22 are each independently a hydrogen atom or a methyl group, and particularly preferably a hydrogen atom. The symbol nb is an integer indicating the number of a repeating unit, and is 0 or 1, and preferably 0. R21 and R22 can be each independently the above group in each repeating unit.

In the formula Is, R31 and R32 are each independently a group selected from the group consisting of a hydrogen atom, a C1-C3 alkyl group, and a C1-C3 alkoxy group. Preferably, R31 and R32 are each independently a hydrogen atom or a methyl group, and particularly preferably a hydrogen atom. The symbol nc is an integer indicating the number of a repeating unit, and is 0, 1, 2, or 3, and preferably 1. R31 and R32 can be each independently the above group in each repeating unit. The sum of nc+nd is an integer of 0 to 3, and preferably 2.

In the formula Is, R41 and R42 are each independently a group selected from the group consisting of a hydrogen atom, a C1-C3 alkyl group, and a C1-C3 alkoxy group. Preferably, R41 and R42 are each independently a hydrogen atom or a methyl group. The symbol nd is an integer indicating the number of a repeating unit, and is 0, 1, 2, or 3, and preferably 1. R41 and R42 can be each independently the above group in each repeating unit.

In the formula Is, Q1 can be a group selected from the group consisting of:
a hydrogen atom;
a phosphate group formed together with O bonded to Q1;
a nucleotide, nucleic acid or peptide nucleic acid linked via a phosphodiester bond formed by a phosphate group formed together with O bonded to Q1; and a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and benzoyl group.

In the formula Is, Q2 can be a group selected from the group consisting of:
a hydrogen atom;
a phosphate group formed together with O bonded to Q2;
a nucleotide, nucleic acid or peptide nucleic acid linked via a phosphodiester bond formed by a phosphate group formed together with O bonded to Q2; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a triethylamine salt (hereinafter referred to as a TEA salt) of —PH(=O)OH, a 1,8-diazabicyclo[5.4.0]undec-7-ene salt (hereinafter referred to as a DBU salt) of —PH(=O)OH, a TEA salt of —PH(=S)OH, and a DBU salt of PH(=S)OH.

The 2-cyanoethyl-N,N-dialkyl(C1-C4)phosphoramidite group has the following structure:

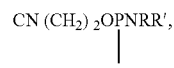

Each of the groups R and R' forming the dialkyl group as described above can be a C1-C4 alkyl group. Examples of such a 2-cyanoethyl-N,N-dialkyl(C1-C4)phosphoramidite group include a 2-cyanoethyl-N,N-dimethylphosphoramidite group, a 2-cyanoethyl-N,N-diethylphosphoroamidite group and a 2-cyanoethyl-N,N-diisopropylphosphoramidite group.

The methylphosphonamidite group has the following structure:

Each of the groups R and R' as described above can be a hydrogen atom or a C1-C4 alkyl group.

The ethylphosphonamidite group has the following structure:

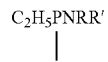

Each of the groups R and R' can be a hydrogen atom or a C1-C4 alkyl group.

The oxazaphospholidine group has the following structure:

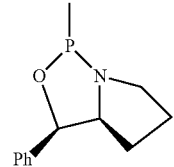

The thiophosphite group has the following structure:

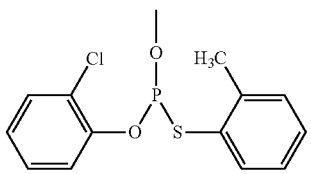 [SMILES: COP(Oc1ccccc1Cl)Sc1ccccc1C]

Each of the TEA salt of —PH(═O)OH and the TEA salt of —PH(═S)OH is a triethylamine (TEA) salt of each.

Each of the DBU salt of —PH(═O)OH and the DBU salt of —PH(═S)OH is a diazabicycloundecene (DBU) salt of each.

In a preferred embodiment, Q1 can be a hydrogen atom.

In a preferred embodiment, Q1 can be a nucleotide or nucleic acid linked via a phosphodiester bond formed by a phosphate group formed together with O bonded to Q1.

In a preferred embodiment, Q1 can be the protecting group as described above, preferably a dimethoxytrityl group, a trityl group, a monomethoxytrityl group, a trimethoxytrityl group, and particularly preferably the dimethoxytrityl group.

In a preferred embodiment, Q2 can be a hydrogen atom.

In a preferred embodiment, Q2 can be a nucleotide or nucleic acid linked via a phosphodiester bond formed by a phosphate group formed together with O bonded to Q2.

In a preferred embodiment, Q2 can be the protecting group as described above, preferably a 2-cyanoethyl-N,N-dialkyl(C1-C4)phosphoramidite group, an oxazaphospholidine group, and a thiophosphite group.

(IIs)

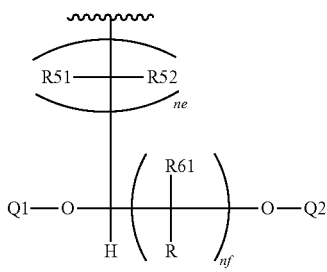

In the formula IIs, R51 and R52 are each independently a group selected from the group consisting of a hydrogen atom, a C1-C3 alkyl group, and a C1-C3 alkoxy group. The symbol ne is an integer indicating the number of a repeating unit and is 1, 2 or 3. R51 and R52 can be each independently the above group in each repeating unit.

In the formula IIs, R61 and R62 are each independently a group selected from the group consisting of a hydrogen atom, a C1-C3 alkyl group, and a C1-C3 alkoxy group. The symbol of is an integer indicating the number of a repeating unit and is 1, 2 or 3. R61 and R62 can be each independently the above group in each repeating unit.

In the formula IIs, Q1 can be Q1 as defined in the above formula Is.

In the formula IIs, Q2 can be Q2 as defined in the above formula Is.

In a preferred embodiment, X can be a group represented by the following formula It:

(It)

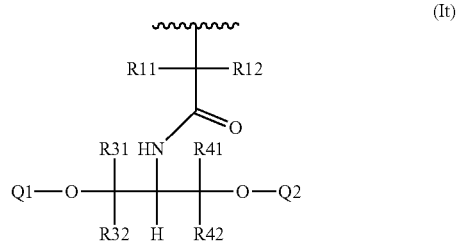

Thus, in a preferred embodiment, in the formula Is, na can be 1, nb can be 0, nc can be 1, and nd can be 1, which can provide the structure of the formula It.

In the formula It, each of R11, R12, R31, R32, R41, R42, Q1, and Q2 can be the group as defined in the above formula Is.

In a preferred embodiment, X can be a group represented by the formula Iu:

(Iu)

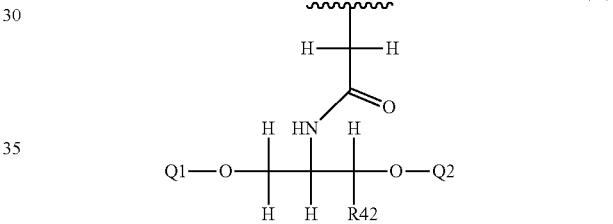

Thus, in a preferred embodiment, in Formula Is, na can be 1, nb can be 0, nc can be 1, and nd can be 1, and each of R11, R12, R31, R32, and R41 can be a hydrogen atom, which can provide the structure of formula Iu.

In the formula Iu, each of R42, Q1, and Q2 can be the group as defined in the above formula Is.

[Modified Nucleic Acid]

In a preferred embodiment, Q1 can be a nucleotide or nucleic acid linked via a phosphodiester bond formed by a phosphate group formed together with O bonded to Q1, and Q2 can be a nucleotide or nucleic acid linked via a phosphodiester bond formed by a phosphate group formed together with O bonded to Q2. That is, the compound represented by the above formula I can be a modified nucleic acid or modified oligonucleotide in which a photoresponsive artificial nucleotide analog having a characteristic structure is incorporated into the sequence. As used herein, the photoresponsive modified nucleic acid and the photoresponsive modified oligonucleotide thus prepared may be collectively referred to as a photoresponsive modified nucleic acid. In the modified nucleic acid according to the present invention, the photoresponsive artificial nucleotide analog having the characteristic structure may be located at the terminal in the sequence. In this case, it will be a modified nucleotide or modified nucleic acid in which only a side of Q1 or Q2 is linked via a phosphodiester bond formed by a phosphate group formed together with O bonded to Q1 or Q2. Alternatively, a peptide nucleic acid can be used in place of the nucleic acid as described above to provide a photoresponsive modified peptide nucleic acid in which the photoresponsive artificial nucleotide analog having the characteristic structure is incorporated into the sequence.

[Skeletal Structure of Compound]

The compound according to the present invention has a skeletal structure represented by the formula I, and does not have a sugar structure of ribose or deoxyribose that should be possessed by a natural nucleoside and nucleotide, in the formula I. Further, the compound according to the invention does not have a base structure of purine bases or pyrimidine bases that should be possessed by a natural nucleoside and nucleotide, in the formula I. In other words, the compound according to the present invention has a chemical structure that does not seem to be structurally analogous to the natural nucleoside and nucleotide. Nevertheless, when the compound according to the present invention is formed as a single-stranded modified nucleic acid, it can form a double helix with a complementary single-stranded nucleic acid. A pyranocarbazole moiety can then form a crosslink by photoreaction.

[Nucleoside Analog]

In a preferred embodiment, each of Q1 and Q2 can be a hydrogen atom. That is, the compound represented by the above formula I can be a photoresponsive artificial nucleoside analog molecule having a characteristic structure.

[Nucleotide Analog]

In a preferred embodiment, Q1 can be a phosphate group formed together with O bonded to Q1, and Q2 can be a hydrogen atom. That is, the compound represented by the above formula I can be a photoresponsive artificial nucleotide analog molecule having a characteristic structure.

[Reagent for Producing Modified Nucleic Acid]

In a preferred embodiment, Q1 can be the protecting group as defined above, and Q2 can be a phosphate group formed together with O bonded to Q2, or a nucleotide or nucleic acid linked via a phosphodiester bond formed by a phosphate group formed together with O bonded to Q2, or the protecting group as defined above. That is, the compound represented by the above formula I can be a producing reagent (synthetic reagent) for the photoreactive modified nucleic acid.

In a preferred embodiment, Q1 can be the protecting group as defined above, and Q2 can be a phosphate group formed together with O bonded to Q2, or the protecting group as defined above. As is well known, the compound having such a structure can be used as a monomer for nucleic acid synthesis, and can be used as a reagent that can be employed by a known DNA synthesizer, for example, a reagent for synthesizing modified nucleic acids (a monomer for synthesizing modified nucleic acids), which can be employed by a phosphoramidite method and an H-phosphonate method.

Further, the structure in which Q1 is the protecting group as defined above and Q2 is a nucleotide or nucleic acid linked via a phosphodiester bond formed by a phosphate group formed together with O bonded to Q2 can be a modified nucleic acid, rather than a so-called monomer. In such a case, it can be used as a producing reagent (synthesizing reagent) for extending the chain length.

Examples of such a reagent for producing photoreactive modified nucleic acids (a reagent for synthesizing photoreactive modified nucleic acids) include the following monomers:

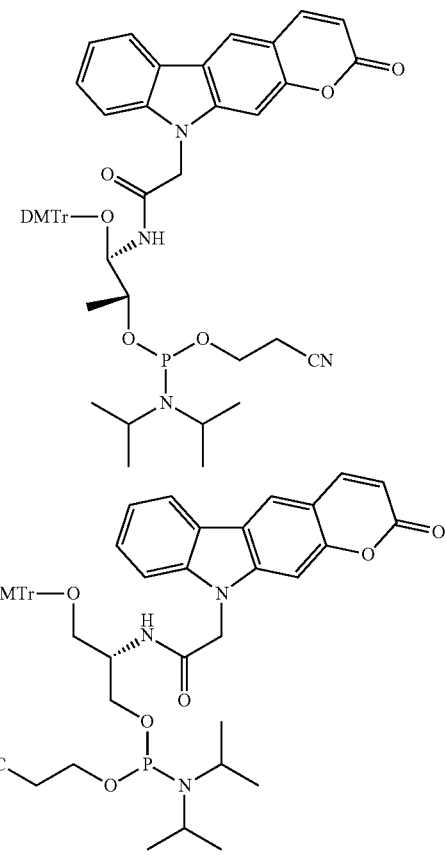

[Photoreactive Crosslinking Agent]

In the compound according to the present invention, the pyranocarbazole moiety can form a crosslink by photoreaction. When the compound according to the present invention is formed as a single-stranded modified nucleic acid, it can form a double helix with a complementary single-stranded nucleic acid, and the pyranocarbazole moiety can form a crosslink by photoreaction, so that a photocrosslink can be formed between the strands formed from one strand of the double helix to the other strand. That is, the compound according to the present invention can be used as a photoreactive crosslinking agent.

[Formation of Photocrosslink]

When the modified nucleic acid according to the present invention is used as a single-stranded nucleic acid, it can hybridize with a complementary single-stranded nucleic acid to form a double helix. In the formation of the double helix, the nucleic acid bases at positions where base pairs should be formed in the complementary strand with the pyranocarbazole structure portion can be freely selected without any particular limitation. When the formed double helix is irradiated with light, a crosslink can be formed by a photoreaction between the nucleic acid strands forming the double helix. The photocrosslink is formed between a nucleic acid base and the pyranocarbazole structural, the nucleic acid base being located at a position where a base pair is formed in the complementary strand, with a nucleic acid base located on the 5' terminal side by one base in the sequence from a position where the pyranocarbazole structural moiety is located as a nucleic acid base. In other words, the photocrosslink is formed between a nucleic acid base and the pyranocarbazole structure, the nucleic acid base being located at the 3' terminal side by one base in the sequence from a nucleic acid base at a position where a base pair should be formed with the pyranocarbazole structure moiety in the complementary strand moiety.

[Base Specificity of Photocrosslinking]

In the present invention, the counterpart base with which the pyranocarbazole structure can form a photocrosslink is a base having a pyrimidine ring. On the other hand, the pyranocarbazole structure does not form a photocrosslink with a base having a purine ring. In other words, the photocrosslinkable compound according to the present invention has specificity that it forms photocrosslinks with cytosine, uracil, and thymine as natural nucleic acid bases, whereas it does not form photocrosslinks with guanine and adenine.

[Sequence Selectivity of Photoreactive Crosslinking Agent]

The photoreactive modified nucleic acid (photocrosslinkable modified nucleic acid) according to the present invention can be photocrosslinked after hybridizing with a sequence having a base sequence complementary to the modified nucleic acid to form a double helix. This can allow photocrosslinking reaction to be performed only on the target specific sequence. In other words, the photoreactive crosslinking agent according to the present invention can impart very high base sequence selectivity by designing a sequence as needed.

[Wavelength of Light Irradiation]

A wavelength of light irradiated for photocrosslinking can be, for example, in a range of from 350 to 600 nm, and preferably in a range of from 400 to 600 nm, and more preferably in a range of from 400 to 550 nm, and even more preferably in a range of from 400 to 500 nm, and still more preferably in a range of from 400 to 450 nm. In a preferred embodiment, single wavelength laser light in these wavelength ranges can be used. Thus, in the present invention, a photocrosslink can be formed by irradiation with light having a wavelength in the visible light region. The conventional photoreactive crosslinking agents require irradiation with light having a wavelength shorter than these ranges. According to the present invention, a photocrosslink can be formed by irradiation with light having a longer wavelength than the conventional photoreactive crosslinking agents, which is advantageous in that adverse effects on nucleic acids and cells due to light irradiation can be minimized.

[Cleavage of Photocrosslink]

According to the compound of the present invention, after forming the photocrosslink, photocleavage can be further carried out by irradiation with light. That is, the photoreactive compound according to the present invention enables reversible photocrosslinking, and can be used as a reversible photoreactive crosslinking agent.

As recalled from the reversibility of the photocrosslinking, the use of the reversible photoreactive crosslinking agent of the compound according to the present invention can allow the nucleic acid having a specific base sequence to be separated, recovered or detected under physiological conditions. Therefore, the present invention also relates to a method for separating, recovering, or detecting a nucleic acid having a desired base sequence using the reversible photoreactive crosslinking agent.

The wavelength of light irradiated for photocleavage can be, for example, in a range of from 300 to 350 nm, and preferably in a range of from 300 to 340 nm. In a preferred embodiment, single wavelength laser light in these wavelength ranges can be used.

[Photoreaction Temperature]

In a preferred embodiment, to proceed with the photocrosslinking reaction, irradiation with light is generally carried out at a temperature in a range from 0 to 50° C., and preferably from 0 to 40° C., and more preferably from 0 to 30° C., and even more preferably from 0 to 20° C., and still more preferably from 0 to 10° C., and still more preferably from 0 to 5° C. In order to proceed with the photocleavage reaction, irradiation with light is generally carried out at a temperature in a range from 55 to 100° C., and preferably from 60 to 90° C., and more preferably from 60 to 80° C.

[Photoreaction Conditions]

Due to the use of photoreaction, the photocrosslinking and photocleavage according to the present invention have no particular restriction on a pH, a salt concentration or the like, and can be carried out by irradiation with light in a solution having a pH and a salt concentration where biopolymers such as nucleic acids can be stably present.

[Photoreaction Time]

The photocrosslinking and photocleavage according to the present invention proceed very rapidly. For example, in a case of psoralen known as a photoreactive compound, the photoreaction requires several hours (by irradiation with light having 350 nm), whereas, in the present invention, the photoreaction proceeds by irradiation with light having a much longer wavelength, for example, for only 10 seconds to 60 seconds (by irradiation with light having 400 nm) to causes photocrosslinking. That is, by using the photocrosslinking agent according to the present invention, the photoreaction can be allowed to proceed by irradiation with light, for example, for 1 to 120 seconds, or 1 to 60 seconds, to form a photocrosslink. Further, according to the photocrosslinking according to the present invention, the photoreaction can be allowed to proceed by irradiation with light, for example, for 1 to 120 seconds or 1 to 60 seconds, using the above wave length and temperature, to cleave the photocrosslink.

[Synthesis Route of Photoresponsive Artificial Nucleoside Analog Molecule]

The photoresponsive artificial nucleoside analog molecule according to the present invention can be synthesized, for example, along a synthesis route shown in Scheme 1 as described below. Scheme 1 includes a procedure of obtaining compound 1, synthesizing compound 4 therefrom, and subjecting it to dehydration condensation reaction with amine to form an amide bond to obtain compound 5.

[Formation of Amide by Dehydration Condensation with Amine]

Thus, according to the synthetic route of Scheme 1, from a modified pyranocarbazole molecule represented by the following formula VI:

(VI)

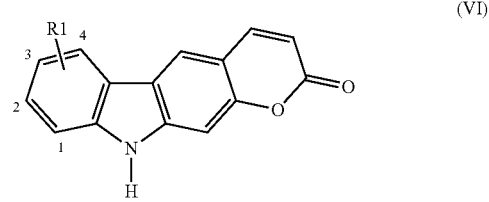

(VI)

in which formula Vi, R1 is the group as defined in the formula I, a carboxylic acid represented by the formula III can be synthesized:

(III)

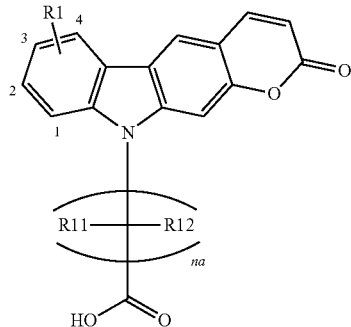

in which formula III:
R1 is the group as defined in the formula VI;
R11 and R12 are the groups as defined in the formula Is; and
na is 1 or 2, and
the carboxylic acid can be subjected to dehydration condensation reaction with an amine represented by the formula IV:

(IV)

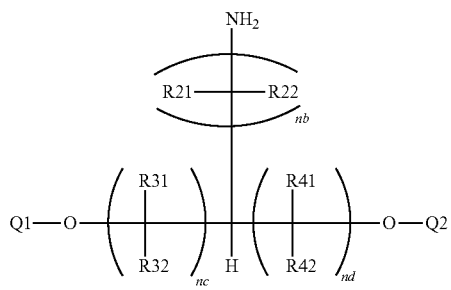

in which formula IV:
R21, R22, R31, R32, R41 and R42 are the groups as defined in the formula Is;
nb is 0 or 1;
nc is 0, 1, 2 or 3, nc+nd is an integer of 0 to 3;
nd is 0, 1, 2 or 3, nc+nd is an integer of 0 to 3;
Q1 is a group selected from the group consisting of:
a hydrogen atom;
a phosphate group formed together with O bonded to Q1;
a nucleotide, nucleic acid or peptide nucleic acid linked via a phosphodiester bond formed by a phosphate group formed together with O bonded to Q1; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;
Q2 is a group selected from the group consisting of:
a hydrogen atom;
a phosphate group formed together with O bonded to Q2;
a nucleotide, nucleic acid or peptide nucleic acid linked via a phosphodiester bond formed by a phosphate group formed together with O bonded to Q2; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH,
to produce a compound represented by the formula V:

(V)

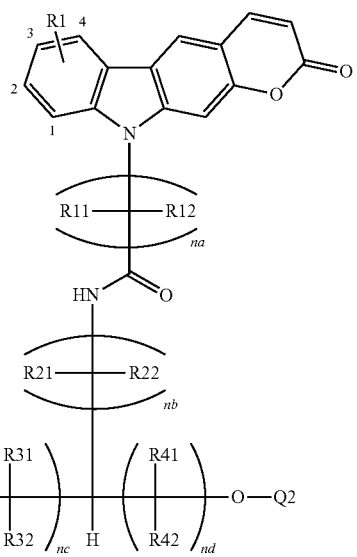

in which formula V:
R1, R11 and R12 are each independently the group as defined above in the formula III;
na is the integer as defined above in the formula III;
R21, R22, R31, R32, R41, R42, Q1 and Q2 are each independently the group as defined above in the formula IV; and
nb, nc, and nd are the integers as defined above in the formula IV.

In a preferred embodiment, as the compound represented by the above formula IV, a compound represented by the following formula VII can be used:

(VII)

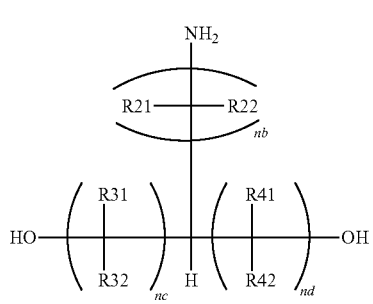

in which formula VII:
R21, R22, R31, R32, R41 and R42 are the groups as defined in the formula Is;
nb is 0 or 1;
nc is 0, 1, 2, or 3, nc+nd is an integer of 0 to 3; and
nd is 0, 1, 2, or 3, and nc+nd is an integer of 0 to 3.

When the compound represented by the following formula VII is used as the compound represented by the above formula IV, the compound represented by the above formula V can be a compound represented by the following formula VIII:

(VIII)

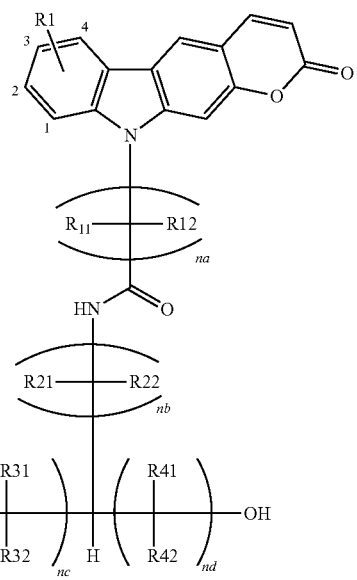

in which formula VIII:
R1 is the group as defined in the formula III;
R11 and R12 are the groups as defined in the formula III;
na is 1 or 2;
R21, R22, R31, R32, R41 and R42 are the groups as defined in the formula VII;
nb is 0 or 1;
nc is 0, 1, 2, or 3, nc+nd is an integer of 0 to 3; and
nd is 0, 1, 2, or 3, and nc+nd is an integer of 0 to 3.

In a preferred embodiment, as the carboxylic acid of the above formula III, a carboxylic acid represented by the formula IIIa can be used:

(IIIa)

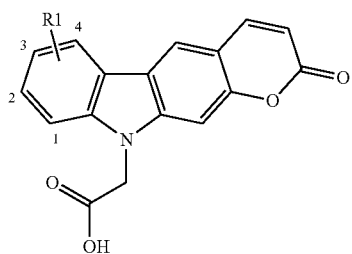

in which formula IIIa, R1 is the group as defined in the formula III.

In a preferred embodiment, as the amine of the above formula VII, an amine represented by the formula VIIa can be used:

(VIIa)

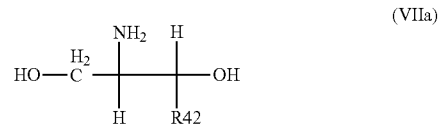

in which formula VIIa, R42 is the group as defined in the formula VII, preferably R42 can be a hydrogen atom or a methyl group.

When the carboxylic acid of the formula IIIa is used as the carboxylic acid of the formula III and the amine of the formula VIIa is used as the amine of the formula VII, the compound of formula VIII can be a compound represented by the formula VIIIa:

(VIIIa)

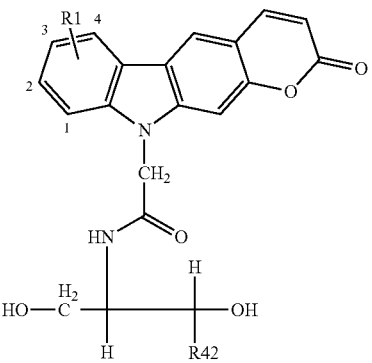

in which formula VIIIa:
R1 is the group as defined in the formula IIIa; and
R42 is the group as defined in the formula VIIa, preferably R42 can be a hydrogen atom or a methyl group.

As described above, the compounds of the formula V, formula VIII, and formula VIIIa can be synthesized by amide formation due to dehydration condensation with the amine. While the synthesis route of Scheme 1 has been described by exemplifying the case where Q1 and Q2 are hydrogen atoms in those formulae, the compound of the formula V can be prepared by amide formation due to dehydration condensation with the amine even if Q1 and Q2 are other than the hydrogen atoms.

The above synthesis route according to the present invention is excellent in that it has few steps, is simple, and can expect a high total yield. Further, when comparing the synthesis route according to the present invention with a conventional synthesis method of a photocrosslinking agent, the former is advantageous in that it does not include any step that requires attention and skill in operations, such as an activation step with hydrogen chloride. That is, in the synthesis of the conventional photoreactive modified nucleoside molecule, the steps in the synthesis route are numerous and complicated, resulting in a lower total yield, as compared with the synthesis route according to the present invention, because the conventional photoreactive modified nucleoside molecule has deoxyribose or ribose in its structure. The synthesis of the conventional photoreactive modified nucleoside molecule includes steps that require attention and skill in operations, such as an activation step with hydrogen chloride, for protecting and activating hydroxyl groups of the sugar, because the conventional photoreactive modified nucleoside molecule has deoxyribose or ribose in its structure. Therefore, the compound according to the present invention is excellent in terms of the ease of synthesis and the higher total yield. The present invention also relates to the above excellent synthesis method (production method).

[Synthesis of Monomer for Synthesizing Modified Nucleic Acid and Modified Nucleic Acid]

Using the photoresponsive artificial nucleoside analog molecule (the compound of the formula VIII or formula VIIIa) obtained by the above synthesis route, a synthesizing monomer (producing reagent) for obtaining the modified nucleic acid according to the present invention can be obtained using a method as shown in Scheme 1 as described below or a method known to one of ordinary skill in the art. The structure of the synthesizing monomer for the modified nucleic acid according to the present invention is as described above. The use of the monomer as a nucleic acid synthesizing reagent by a known method such as a phosphoramidite method and an H-phosphonate method can provide a nucleic acid or oligonucleotide in which the photoresponsive artificial nucleoside analog molecule (the compound of the formula VIII or the formula VIIIa) is incorporated into the sequence (the modified nucleic acid according to the present invention) or a peptide nucleic acid. Thus, the synthesizing monomer for the modified nucleic acid according to the present invention is excellent in that it can be used as a nucleic acid synthesizing reagent in known techniques such as the phosphoramidite method and the H-phosphonate method.

EXAMPLES

Hereinafter, the present invention will be described in detail with reference to Examples. The present invention is not limited to Examples illustrated below.

[Synthesis of pc-D-phosphoramidite]

A photoresponsive artificial nucleoside analog molecule (compound 5) having a D-threoninol structure (which may be referred to as a nucleoside analog or a photoreactive element) was synthesized along a synthesis route at six steps, as shown in the following Scheme 1, and a synthesizing monomer for a modified nucleic acid (compound 7) was further synthesized.

Scheme 1

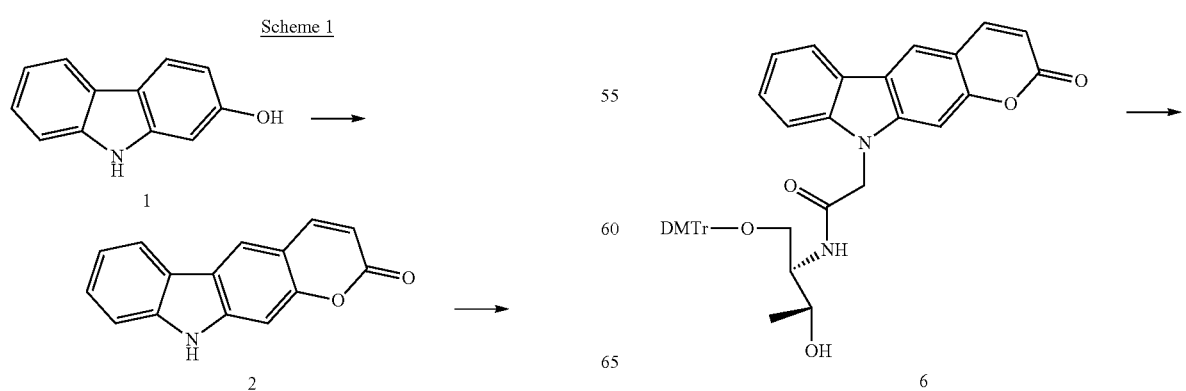

-continued

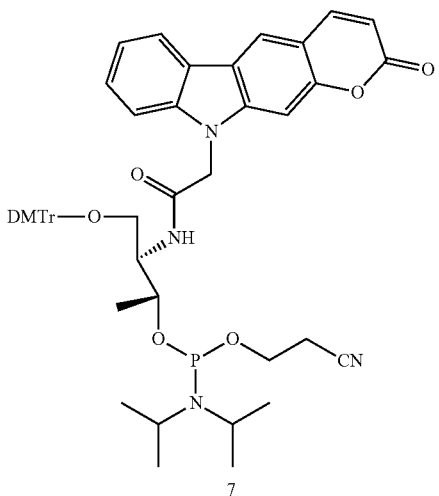

7

(1) Synthesis of Compound 2

In accordance with Non-Patent Document (Synthesis of fused pyranocarbazolones with biological interest, A. Vronteli et al., Commemorative Issue in Honor of Prof. Michael Orfanopoulos on the occasion of his outstanding contributions to organic synthetic chemistry, Volume 2015, Issue 3, pp. 111-123), pyranocarbazole (compound 2) was synthesized from 2-hydroxycarbazole (compound 1).

(2) Synthesis of Compound 3

Acetonitrile (1000 ml) was introduced into a flask charged with compound 2 (4.7 g) and sodium hydroxide (2.4 g), and stirred at room temperature for one hour, and ethyl bromoacetate (6.67 g) was then added dropwise and further stirred for one hour. Residual sodium hydroxide was removed by suction filtration with a Nutsche type filtration device, and the resulting filtrate was concentrated with a rotary evaporator. The resulting compound 3 (solid) was directly used in the next step. NMR measurement was performed using the resulting compound, the assignment of each peak was determined, and the structure of the compound was confirmed.

1H-NMR (300 MHz, CDCL$_3$): 8.14-7.21 (m, 6H, ArH), 7.88 (d, 1H, O=C—CH=CH), 6.34 (d, 1H, O=C—CH=CH), 4.99 (s, 2H, CH$_2$CO), 4.24 (q, 2H, CH$_3$CH$_2$), 1.27 (t, 3H, CH$_3$)

(3) Synthesis of Compound 4

Compound 3 obtained in the previous step was dissolved in THF (1000 ml). An aqueous solution of sodium hydroxide (0.9 g) dissolved in water (50 ml) was added dropwise to the above THF solution and stirred at room temperature for 3 hours. After the end of reaction, the reaction solution was neutralized with dilute hydrochloric acid so as to have a pH of from 6 to 7. The reaction solution was concentrated with a rotary evaporator, and a target product was extracted into an organic phase by a liquid separation operation using ethyl acetate. The organic layer was concentrated by a rotary evaporator to obtain compound 4 (solid). The resulting compound 4 was directly used in the next step. NMR measurement was performed using the resulting compound, the assignment of each peak was determined, and the structure of the compound was confirmed.

1H-NMR (300 MHz, DMSO): 8.48-7.30 (m, 6H, Ar—H), 8.18 (d, 1H, O=O—CH=CH), 6.35 (d, 1H, O=C—CH=CH), 5.30 (s, 2H, CH$_2$CO)

(4) Synthesis of Compound 5 (Threoninol Skeleton Type Pyranocarbazole Nucleoside Analog: pc-D)

Compound 4 obtained in the previous step, 1-hydroxybenzotriazole (2.7 g), 1-(3-dimethylaminopropyl)-3-ethylcarbodiimide hydrochloride (3.8 g), and D-threoninol (2.1 g) were charged into a flask, purged with nitrogen and then dissolved in DMF (100 ml), and stirred at room temperature for 2 hours. A saturated aqueous sodium hydrogen carbonate solution was added while stirring the reaction mixture. The produced precipitate was subjected to suction filtration by a filtering device with a glass filter. The precipitate was washed with distilled water and hexane, and then dried to obtain compound 5 (solid). A UV-vis spectrum of the resulting compound 5 was measured by a spectrophotometer (FIG. 1). Characteristic absorption peaks appeared at 250 to 400 nm, confirming that compound 5 had a pyranocarbazole structure. Moreover, NMR measurement was implemented using the resulting compound, the assignment of each peak was determined, and the structure of the compound was confirmed.

1H-NMR (300 MHz, DMSO): 8.48-7.29 (m, 6H, Ar—H), 8.19 (d, 1H, O=C—CH=CH), 8.03 (d, 1H, NHCO), 6.34 (d, 1H, O=C—CH=CH), 5.17 (s, 2H, CH$_2$CO), 4.75 (br, 1H, CH$_2$OH), 4.68 (br, 1H, CHOH), 3.91 (br, 1H, NHCH), 3.64 (m, 1H, CH$_2$OH), 3.51 (m, 1H, CH$_2$OH), 1.03 (d, 3H, CH$_3$)

(5) Synthesis of Compound 6

Compound 5 (4.6 g) and 4-dimethylaminopyridine (0.3 g) were charged into a flask and purged with nitrogen. Pyridine (55 ml) was then added and dissolved while cooling in an ice water bath. 4,4'-Dimethoxytrityl chloride (8.3 g) was added, stirred for one hour in the ice water bath and allowed to react. The reaction mixture was concentrated by a rotary evaporator and the concentrate was purified by flash chromatography to provide compound 6. NMR measurement was performed using the resulting compound, the assignment of each peak was determined, and the structure of the compound was confirmed. 1H-NMR (300 MHz, CDCL$_3$): 8.13-7.03 (m, 11H, Ar—H), 7.85 (d, 1H, O=C—CH=CH), 6.95-6.69 (m, 8H, MeO—Ar—H), 6.33 (d, 1H, O=C—CH=CH), 6.29 (d, 1H, NHCO), 4.96 (s, 2H, CH$_2$CO), 3.88 (m, 1H, NCH), 3.88 (m, 1H, CHOH), 3.77 (s, 6H, OCH$_3$), 3.25-3.12 (m, 2H, CH$_2$—ODMTr), 2.52 (m, 1H, CHOH), 0.93 (d, 3H, CH$_3$)

(6) Synthesis of Compound 7 (pc-D-phosphoramidite)

Compound 6 (7.2 g) and 5-benzylthio-1H-tetrazole (0.2 g) were charged into a flask, purged with nitrogen. Acetonitrile (160 ml) was then added and dissolved in an ice water bath. 2-Cyanoethyl N,N,N',N'-tetraisopropylphosphoramidite (5.3 g) was added and stirred at room temperature for 2 hours. The reaction mixture was concentrated by a rotary evaporator, and the resulting concentrate was purified by flash chromatography to provide compound 7. NMR measurement was performed using the resulting compound, the assignment of each peak was determined, and the structure of the compound was confirmed.

1H-NMR (600 MHz, CDCL$_3$): 8.12-7.18 (m, 11H, Ar—H), 7.86 (d, 1H, O=O—CH=CH), 7.12-6.71 (m, 8H, MeO—Ar—H), 6.34 (d, 1H, O=C—CH=CH), 5.87 (d, 1H, NHCO), 4.93 (s, 2H, CH$_2$CO), 4.22 (m, 1H, CHOP), 4.12 (q, 2H, NC—CH$_2$—CH$_2$), 4.07 (m, 1H, NHCH), 3.77 (s, 6H, OCH$_3$), 3.00 (m, 2H, CH$_2$O-DMTr), 2.10-2.00 (m, 2H, N—CH—(CH$_3$)$_2$), 1.26 (t, 2H, NC—CH$_2$), 1.06-0.43 (m, 12H, N—CH—(CH$_3$)$_2$), 0.93 (d, 3H, CH$_3$)

[Synthesis of Oligo DNA Containing Photoreactive Element (Pc-D)]

According to the general cyanoethyl phosphoramidite method, an oligo DNA containing a photoreactive element (which may be referred to as a nucleic acid photoreactive element) was synthesized by an automatic DNA synthesizer. Only for a solid-phase condensation reaction of Compound 7, a reaction time was set to 999 seconds. A coupling yield of compound 7 as measured by a tritylyl monitor was 98% or more. After release and deprotection from the solid phase using an aqueous solution containing 28% by mass of ammonia, purification was carried out by reverse phase HPLC to provide an oligo DNA containing the target nucleic acid photoreactive element (5'-TGCAXCCGT-3', in which X is the nucleic acid photoreactive element (pc-D))(SEQ ID NO: 1). The oligo DNA was identified by MALDI-TOF MS analysis. ([(M+H)+]; Calcd. 2827.80, Found 2828.94).

An oligo DNA containing a nucleic acid photoreactive element (5'-TGCGXCCGT-3-', in which X is the nucleic acid photoreactive element (pc-D)) (SEQ ID NO: 3) was obtained by the same procedure as that described above, with the exception that the DNA sequence was partially changed and inputted into the automatic DNA synthesizer.

[Synthesis of Pc-S-Phosphoramidite and Pc-S-Containing DNA]

A photoresponsive artificial nucleoside analog (compound 8) (pc-S) corresponding to a structure obtained by replacing threoninol with serinol (2-amino-1,3-propanediol) in the above synthesized pc-D was synthesized along a synthesis route at six steps (which were the same as those of pc-D, until compound 4), as represented by the following Scheme 2. Further, a synthesizing monomer for a modified nucleic acid (compound 10) was synthesized.

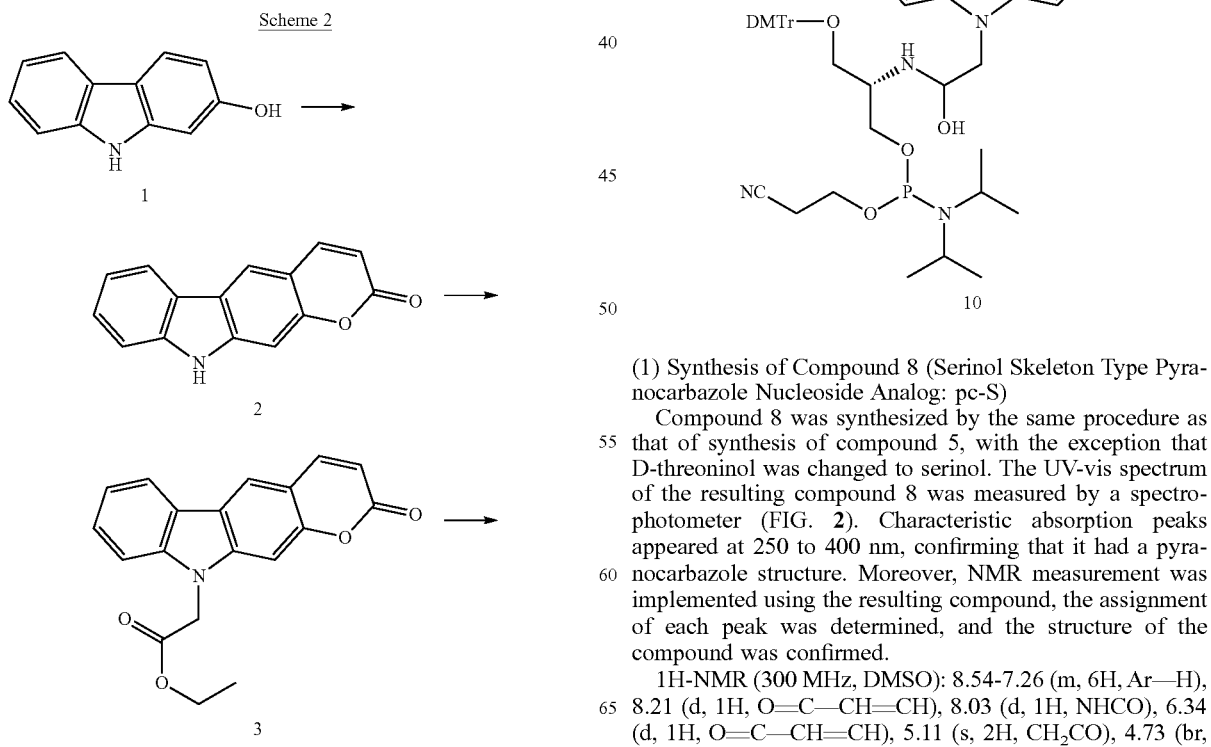

(1) Synthesis of Compound 8 (Serinol Skeleton Type Pyranocarbazole Nucleoside Analog: pc-S)

Compound 8 was synthesized by the same procedure as that of synthesis of compound 5, with the exception that D-threoninol was changed to serinol. The UV-vis spectrum of the resulting compound 8 was measured by a spectrophotometer (FIG. 2). Characteristic absorption peaks appeared at 250 to 400 nm, confirming that it had a pyranocarbazole structure. Moreover, NMR measurement was implemented using the resulting compound, the assignment of each peak was determined, and the structure of the compound was confirmed.

1H-NMR (300 MHz, DMSO): 8.54-7.26 (m, 6H, Ar—H), 8.21 (d, 1H, O=C—CH=CH), 8.03 (d, 1H, NHCO), 6.34 (d, 1H, O=C—CH=CH), 5.11 (s, 2H, CH$_2$CO), 4.73 (br, 2H, CH$_2$OH), 3.75 (br, 1H, NHCH), 3.43 (m, 4H, CH$_2$OH)

(2) Synthesis of Compound 9 and Compound 10 (Pc-S-Phosphoramidite)

Synthesis of Compound 9 and Compound 10 (Pc-S-Phosphoramidite) was Carried Out by the Same Method as that of Synthesis of Compound 6 and Compound 7 in Scheme 1.

[Synthesis of Oligo DNA Containing Photoreactive Element (Pc-S)]

Using compound 10, an oligo DNA containing a nucleic acid photoreactive element (5'-TGCAXCCGT-3', in which X is the nucleic acid photoreactive element (pc-S))(SEQ ID NO: 5) was obtained by the same procedure as that of pc-D-phosphoramidite.

[Evaluation of Photoreactivity of pc-D]

To an equal amount mixture (5 µM in 50 mM Na-Cacodylate buffer (pH 7.4), 100 mM NaCl) of the oligo DNA containing pc-D [hereinafter referred to as ODN (Y·pc-D), in which Y is A (adenine) or G (guanine)] and a complementary oligo DNA [hereinafter referred to as ODN (Z), in which Z is T (thymine) or C (cytosine)] was added deoxyuridine (25 µM) as an internal standard, and irradiated with light at 4° C. (400 nm, 9500 mW/cm$^2$). The solution was analyzed by HPLC (eluent: acetonitrile/50 mM of ammonium formate; 1-20% of acetonitrile/10 min; a flow rate: 0.2 mL/min) to evaluate photoreactivity.

(1) Photocrosslinking Reaction Targeted for Thymine

FIG. 3a is an explanatory diagram showing the flow of the operations. In the ODN (A-pc-D)(5'-TGCAXCCGT-3') (SEQ ID NO: 1) in which the target of photocrosslinking is thymine (T). the nucleoside analog (pc-D) according to the present invention is introduced as an improved photoreactive element at a position of X in the sequence.

FIG. 3b shows analysis results obtained by irradiating ODN (A-pc-D) and a complementary oligo DNA, ODN(T) (5'-ACGGGTGCA-3') (SEO ID NO: 2) with light having 400 nm using a UV-LED irradiation device (OmniCure® LX405S) from U-VIX and then conducting analysis by HPLC. Charts arranged in the vertical axis direction correspond to light irradiation times (0 sec, 1 sec, 5 sec. 10 sec, and 30 sec), and the horizontal axis indicates a retention time (minutes). The peaks of ODN (A•pc-D) and ODN (T), which were present before light irradiation (0 sec), were reduced by the light irradiation, and at the same time, a peak of a photodimer (ODN (pc-D/T)) with ODN (A•pc-D) and ODN (T) crosslinked appeared. As the light irradiation time increased, the peak area of(ODN (pc-D/T)) increased, confirming that the photocrosslinking reaction was progressing. FIG. 3c is a graph showing a change in a crosslinking rate as a function of light irradiation time. In FIG. 3c, the horizontal axis represents a light irradiation time (seconds), and the vertical axis represents a conversion rate (%). The conversion rate, i.e., a rate of change from a monomer to a dimer, was defined as a conversion rate of 100% for a case of being completely changed to the dimer. The nucleoside analog according to the present invention or ODN (A•pc-D) showed a high conversion rate of 94% after 10 seconds of irradiation, and substantially 100% crosslinking was achieved after one hour.

FIG. 3d also shows HPLC analysis results in a case where using ODN (A·pc-D) and ODN (T), irradiation was carried out with light having 450, 500, and 550 nm for one hour using a CRM-FD type irradiation spectrometer from JASCO Corporation. The respective conversion rates were 86% at 450 nm, 70% at 500 nm, and 38% at 550 nm.

(2) Photocrosslinking Reaction Targeted for Cytosine

The photocrosslinking reaction was carried out by the same procedure as that of ODN (A•pc-D), using a pc-D-containing oligo DNA in which C (cytosine) was a target for the photocrosslinking (5'-TGCGXCCGT-3'; hereinafter referred to as ODN (G-pc-D)) (SEQ ID NO: 3) and a complementary oligo DNA (5'-ACGGGCGCA-3': hereinafter referred to as ODN (C))(FIG. 4a)(SEQ ID NO: 4). As a result of irradiation with light having 400 nm for 30 seconds, the conversion rate by photocrosslinking was 71% (FIG. 4b).

[Photocleavage Reaction of Photocrosslinked Product of pc-D]

A photodimer ODN (pc-D/T) solution prepared by light irradiation (400 nm, 60 seconds) of a mixed solution of ODN (A·pc-D) and ODN (T) was heated at 60° C., and irradiated with light having 312 nm for 0 minutes, 5 minutes, and 30 minutes using 15 W transilluminator (FIG. 5a). By light irradiation, the peak of ODN (pc-D/T) decreased, and the original ODN (A·pc-D) and ODN (T) peaks appeared. After 30 minutes of irradiation, the ODN (pc-D/T) peak disappeared and the conversion rate was 100% (FIG. 5b).

[Evaluation of Photoreactivity of Pc-S]

The photocrosslinking reaction was carried out by the same procedure as that of ODN (A-pc-D), using a pc-S-containing oligo DNA in which T (thymine) was a target for the photocrosslinking (5'-TGCAXCCGT-3': hereinafter referred to as ODN (A-pc-S)) (SEQ ID NO: 5), and ODN (T) which was a complementary oligo DNA (FIG. 6a).

FIG. 6b shows results of analysis by HPLC after irradiation with light having 400 nm for 60 seconds using a UV-LED irradiation device (OmniCure® LX405S) from U-VIX. Charts arranged in the vertical axis direction correspond to light irradiation times (0 seconds, 60 seconds), respectively, and the horizontal axis indicates a retention time (minutes). Peaks of ODN (A·pc-S) and ODN (T), which were present before the light irradiation (0 seconds), were decreased by light irradiation, and at the same time a peak of the photodimer (ODN (pc-S/T) appeared.

[Study for Effect of Irradiation Light Wavelength on Cells]

The following experiment was conducted in order to study that light irradiation at a longer wavelength is caused less damage to cells than light irradiation at a shorter wavelength.

100 µL of 5×10$^5$ cells/ml of cells (GFP-HeLa cells, human cervical cancer-derived strain) was dispensed into a 96-well plate and cultured in a $CO_2$ incubator for 48 hours. Subsequently, light irradiation was carried out using light having a wavelength of 366 nm, 400 nm, or 450 nm, and 10 µL of cell counting kit was then added to each well and colored in the $CO_2$ incubator for 4 hours. An absorbance at 450 nm was then measured using a microplate reader to calculate cell viability. The results are summarized in FIG. 7.

[Result]

FIG. 7 is a graph comparing the light irradiation time (seconds) with the cell viability (%) at each wavelength. This result demonstrates that the cell viability is greatly reduced by light irradiation at 366 nm even for several seconds, whereas the cell viability is not almost reduced at 400 nm and 450 nm, even if light irradiation is carried out for several tens of seconds. That is, this also reveals that pyranocarbazole can be manipulated by long-wavelength light with less cytotoxicity.

INDUSTRIAL APPLICABILITY

The present invention provides a novel compound serving as a photoreactive crosslinking agent that can be used in nucleic acid photoreaction techniques. The present invention is industrially useful.

What is claimed is:

1. A compound represented by the following formula I:

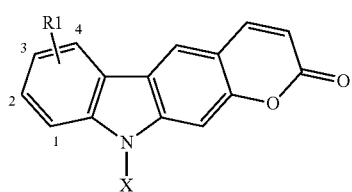

in which formula I:
R1 is a group selected from the group consisting of a hydrogen atom, a halogen atom, a methyl group, a fluorine-substituted methyl grow, an ethyl group, a fluorine-substituted ethyl group, and a C1-C3 alkylsulfanyl group;
X is a group represented by the following formula Is or IIs:

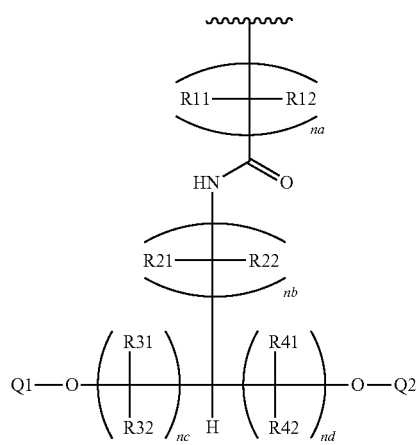

in which formula Is:
R11 and R12 are each independently a group selected from the group consisting of a hydrogen atom, a C1-C3 alkyl group, and a C1-C3 alkoxy group;
na is 1 or 2;
R21 and R22 are each independently a group selected from the group consisting of a hydrogen atom, a C1-C3 alkyl group, and a C1-C3 alkoxy group;
nb is 0 or 1;
R31 and R32 are each independently a group selected from the group consisting of a hydrogen atom, a C1-C3 alkyl group, and a C1-C3 alkoxy group;

nc is 0, 1, 2 or 3, and nc+nd is an integer of 0 to 3;
R41 and R42 are each independently a group selected from the group consisting of a hydrogen atom, a C1-C3 alkyl group, and a C1-C3 alkoxy group;
nd is 0, 1, 2 or 3, and nc+nd is an integer of 0 to 3;
Q1 is a group selected from the group consisting of:
 a hydrogen atom:
 a phosphate group formed together with O bonded to Q1;
 a nucleotide, nucleic acid or peptide nucleic acid linked via a phosphodiester bond formed by a phosphate group formed together with O bonded to Q1; and
 a protecting group selected from:
  a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;
Q2 is a group selected from the group consisting of:
 a hydrogen atom;
 a phosphate group formed together with O bonded to Q2;
 a nucleotide, nucleic acid or peptide nucleic acid linked via a phosphodiester bond formed by a phosphate group formed together with O bonded to Q2; and
 a protecting group selected from:
  a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH; or

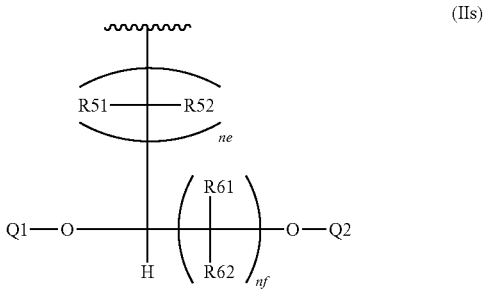

in which formula Is:
R51 and R52 are each independently a group selected from the group consisting of a hydrogen atom, a C1-C3 alkyl group, and a C1-C3 alkoxy group;
ne is 1, 2 or 3;
R61 and R62 are each independently a group selected from the group consisting of a hydrogen atom, a C1-C3 alkyl group, and a C1-C3 alkoxy group;

nf is 0, 1, 2 or 3;

Q1 is a groups selected from the group consisting of:
- a hydrogen atom;
- a phosphate group formed together with O bonded to Q1;
- a nucleotide, nucleic acid or peptide nucleic acid linked via a phosphodiester bond formed by a phosphate group formed together with O bonded to Q1; and
- a protecting group selected from:
  - a trityl group, a monomethoxytrityl group, a dimethoxytrityl group, a trimethoxytrityl group, a trimethylsilyl group, a triethylsilyl group, a t-butyldimethylsilyl group, an acetyl group, and a benzoyl group;

Q2 is group selected from the group consisting of:
- a hydrogen atom;
- a phosphate group formed together with O bonded to Q2;
- a nucleotide, nucleic acid or peptide nucleic acid linked via a phosphodiester bond formed by a phosphate group formed together with O bonded to Q2; and
- a protecting group selected from:
  - a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH.

2. The compound according to claim 1, wherein X is a group represented by the following formula It:

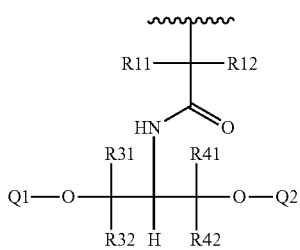

(It)

in which formula It:
- R11 and R12 are each independently the group as defined in the formula Is;
- R31 and R32 are each independently the group as defined in the formula Is;
- R41 and R42 are each independently the group as defined in the formula Is; and
- Q1 and Q2 are the groups as defined in the formula Is.

3. The compound according to claim 1, wherein X is a group represented by the following formula Iu:

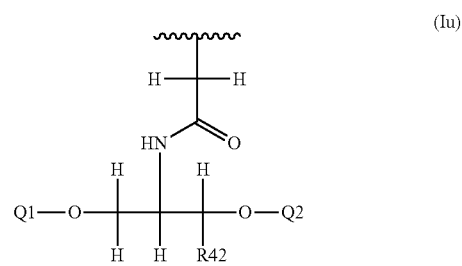

(Iu)

in which formula Iu:
- R42 is the group as defined in the formula Is; and
- Q1 and Q2 are the groups as defined in the formula Is.

4. The compound according to claim 3, wherein R42 is a hydrogen atom or a methyl group.

5. A photoreactive crosslinking agent, comprising the compound according to claim 1.

6. A reagent for producing photoreactive modified nucleic acids, comprising the compound according to claim 1.

7. A method for forming a photocrosslink between a photoreactive crosslinking agent and a nucleic acid base having a pyrimidine ring, comprising:
- hybridizing the photoreactive crosslinking agent comprising the compound according to claim 1 and the nucleic acid base having the pyrimidine ring, and
- irradiating the photoreactive crosslinking agent and the nucleic acid base having the pyrimidine ring with light.

8. A method for producing a compound represented by the following formula V, comprising subjecting a compound represented by the following formula III:

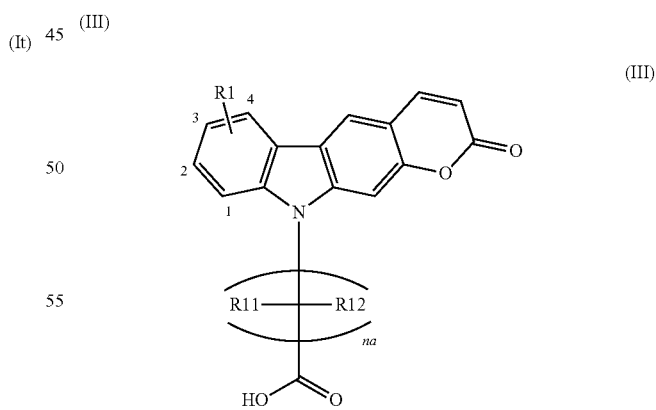

(III)

in which formula III:
- R1 is a group selected from the group consisting of a hydrogen atom, a halogen atom, a methyl group, a fluorine-substituted methyl group, an ethyl group, a fluorine-substituted ethyl group, and a C1-C3 alkylsulfanyl group;

R11 and R12 are each independently a group selected from the group consisting of a hydrogen atom, a C1-C3 alkyl group, and a C1-C3 alkoxy group; and
na is 1 or 2,
to dehydration condensation with a compound represented by the formula IV:

(IV)

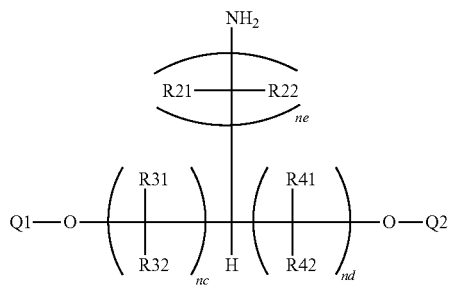

in which formula IV:
R21 and R22 are each independently a group selected from the group consisting of a hydrogen atom, a C1-C3 alkyl group, and a C1-C3 alkoxy group;
nb is 0 or 1;
R31 and R32 are each independently a group selected from the group consisting of a hydrogen atom, a C1-C3 alkyl group, and a C1-C3 alkoxy group,
nc is 0, 1, 2 or 3, and nc+nd is an integer of 0 to 3;
R41 and R42 are each independently a group selected from the group consisting of a hydrogen atom, a C1-C3 alkyl group, and a C1-C3 alkoxy group;
nd is 0, 1, 2 or 3, and nc+nd is an integer of 0 to 3;
Q1 is a group selected from the group consisting of:
a hydrogen atom;
a phosphate group formed together with O bonded to Q1;
a nucleotide, nucleic acid or peptide nucleic acid linked via a phosphodiester bond formed by a phosphate group formed together with O bonded to Q1; and
a protecting group selected from:
a trityl group, a monomethoxytrityl group, a dimethoxytrityl group, a trimethoxytrityl group, a trimethylsilyl group, a triethylsilyl group, a t-butyldimethylsilyl group, an acetyl group, and benzoyl group;
Q2 is a group selected from the group consisting of:
a hydrogen atom;
a phosphate group formed together with O bonded to Q2;
a nucleotide, nucleic acid or peptide nucleic acid linked via a phosphodiester bond formed by a phosphate group formed together with O bonded to Q2; and
a protecting group selected from:
a 2-cyanoethyl-N,N-dialkyl(C1-C4)phosphoramidite group, a methylphosphonamidite group, an ethylphosphonamidite group, an oxazaphospholidine group, a thiophosphite group, a TEA salt of —PH(=O)OH, a DBU salt of —PH(=O)OH, a TEA salt of —PH(=S)OH, and a DBU salt of —PH(=S)OH,
to provide a compound represented by the formula V:

(V)

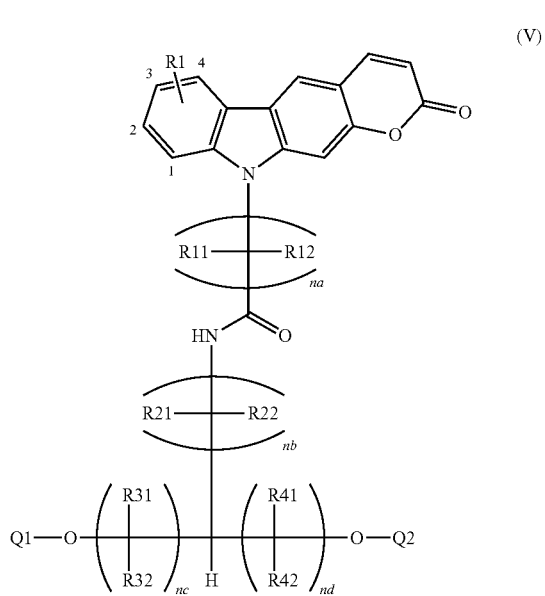

in which formula V:
R1, R11 and R12 are each independently the group as defined in the formula III;
na is the integer as defined in the formula III;
R21, R22, R31, R32, R41, R42, Q1 and Q2 are each independently the group as defined in the formula IV; and
nb, nc, and nd are each independently the integer as defined in the formula IV.

9. The compound according to claim 1,
wherein R1 is a group selected from the group consisting of a hydrogen atom, a halogen atom, a methyl group, an ethyl group, and a C1-C3 alkylsulfanyl group.

10. The method according to claim 8,
wherein R1 is a group selected from the group consisting of a hydrogen atom, a halogen atom, a methyl group, an ethyl group, and a C1-C3 alkylsulfanyl group.

* * * * *